United States Patent
Blanco et al.

(10) Patent No.: US 11,286,249 B2
(45) Date of Patent: Mar. 29, 2022

(54) PYRROLIDINE COMPOUNDS

(71) Applicant: Eli Lilly and Company, Indianapolis, IN (US)

(72) Inventors: Celia Lafuente Blanco, San Sebastian de los Reyes (ES); Nuria Diaz Buezo, Madrid (ES); Jose Antonio Martinez Perez, Madrid (ES); Gema Consuelo Sanz Gil, Madrid (ES); Julian Priego Soler, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/056,144

(22) PCT Filed: Jun. 3, 2020

(86) PCT No.: PCT/US2020/035825
§ 371 (c)(1),
(2) Date: Nov. 17, 2020

(87) PCT Pub. No.: WO2020/247429
PCT Pub. Date: Dec. 10, 2020

(65) Prior Publication Data
US 2021/0253559 A1    Aug. 19, 2021

(30) Foreign Application Priority Data
Jun. 7, 2019    (EP) ...................................... 19382477

(51) Int. Cl.
*C07D 403/14*    (2006.01)

(52) U.S. Cl.
CPC .................................. *C07D 403/14* (2013.01)

(58) Field of Classification Search
CPC .................................................... C07D 403/14
See application file for complete search history.

(56) References Cited

FOREIGN PATENT DOCUMENTS

| EP | 1452521 | 9/2004 |
| WO | 2005/068410 | 7/2005 |
| WO | 2005/068412 | 7/2005 |

OTHER PUBLICATIONS

International Search Report of the International Searching Authority pertaining to International Application No. PCT/US2020/035825; dated Sep. 11, 2020; 6 pages.

(Continued)

*Primary Examiner* — Patricia L Morris
(74) *Attorney, Agent, or Firm* — Macharri Vorndran-Jones

(57) ABSTRACT

The present invention provides compounds of the Formula wherein L is selected from the group consisting of —CH$_2$NHCH$_2$—, —CH$_2$NH—, —NH—, —S—, —S(O)—, —S(O)$_2$—, —O—, —OCH$_2$—, —OCH$_2$CH$_2$O—, —NHSO$_2$NH—, and or a pharmaceutically acceptable salt thereof; a compound of the formula:

(Continued)

processes for preparing the compounds and their salts, a pharmaceutical composition, and methods of treating patients in need of such treatment.

16 Claims, No Drawings

(56) References Cited

OTHER PUBLICATIONS

Written Opinion of the International Searching Authority pertaining to International Application No. PCT/US2020/035825; dated Sep. 11, 2020; 9 pages.

Jin Jing Yi et al., °*Synthesis and Structure Determination of (2S, 2"S)-3-Phenyl-2-(pyrrolidin-2'-yl)-propionic Acid*, Synthetic Communications,vol. 33, No. 22, Aug. 18, 2006 (Aug. 18, 2006), pp. 3913-3917, XP055726631, Philadelphia, PA; US ISSN: 0039-7911, DOI:10.1081/SCC-120026314, Scheme 1, Compound 3.

PYRROLIDINE COMPOUNDS

This application claims priority to 371 international application serial number PCT/US2020/035825, filed Jun. 3, 2020, which claims priority to, EP priority application, 19382477.8, filed Jun. 7, 2019, the contents of which are each hereby incorporated by reference in their entirety.

This invention relates to Pyrrolidine compounds, pharmaceutically acceptable salts thereof, pharmaceutical compositions, and therapeutic uses of the compounds.

There have been significant advances in treating cardiovascular disease (CVD). Despite treatment advances, patients continue to experience cardiovascular disease events such as angina, myocardial infarction, and stroke, which if untreated, lead to death. Lipid disorder or dyslipidemia remains a major risk factor for CVD. Lipid disorders can be divided into four general risk factors: elevated low-density lipoprotein cholesterol (LDL-c), low high-density lipoprotein cholesterol (HDL-c), elevated triglycerides (TG), and elevated lipoprotein(a) (Lp(a)). There are a variety of treatment regimens targeting elevated LDL-c, low HDL-c, and elevated triglycerides. There are few approved treatment options for patients with elevated Lp(a) concentrations. In some cases, apheresis may be used to filter the blood to remove LDL and Lp(a); however, the effects are temporary and typically need to be repeated every two weeks. There is no pharmaceutical treatment approved to lower Lp(a) levels. The physiological function of Lp(a) is complex; however, it is reported that elevated Lp(a) plasma level is an independent risk factor for CVD. There is a need for a pharmaceutical treatment for patients with elevated Lp(a)1.

Additional treatment options are desired for patients suffering from cardiovascular diseases and, in particular, patients suffering from lipid disorders or dyslipidemia. There is a need for additional treatment options for patients whose cardiovascular risks are not adequately managed using current standard of care therapies, such as, diet, exercise and/or the use of one or more drugs such as statins, fibrates, and niacin. The present invention offers another treatment option for patients suffering from CVD. There is a need for pharmaceutically acceptable compounds and treatment options to reduce plasma Lp(a) levels.

Provided is a compound of formula I':

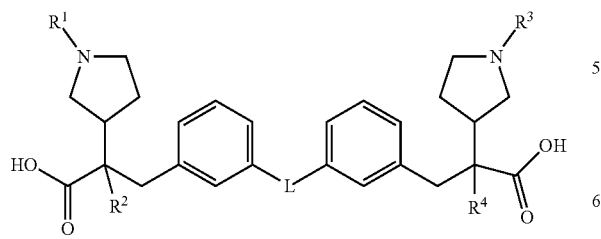

wherein

L is selected from the group consisting of —CH$_2$NHCH$_2$—, —CH$_2$NH—, —NH—, —S—, —S(O)—, —S(O)$_2$—, —O—, —OCH$_2$—, —OCH$_2$CH$_2$O—, —NHSO$_2$NH—,

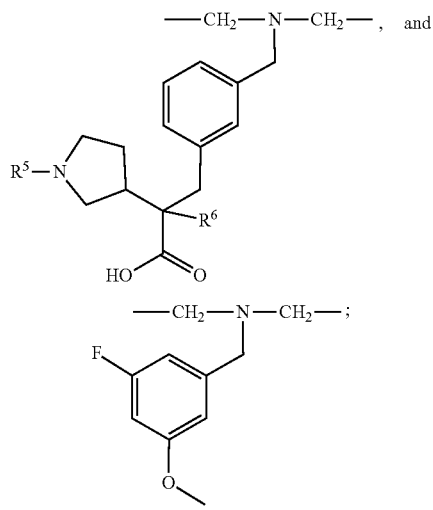

$R^1$, $R^2$, $R^3$, $R^4$, $R^5$, and $R^6$ are each independently selected from the group consisting of H and CH$_3$; or a pharmaceutically acceptable salt thereof.

Provided is a compound of formula I":

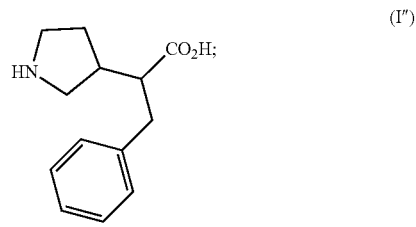 [SMILES: O=C(O)C(Cc1ccccc1)C1CCNC1]

or a pharmaceutically acceptable salt thereof.

Provided is a compound of the Formula 1:

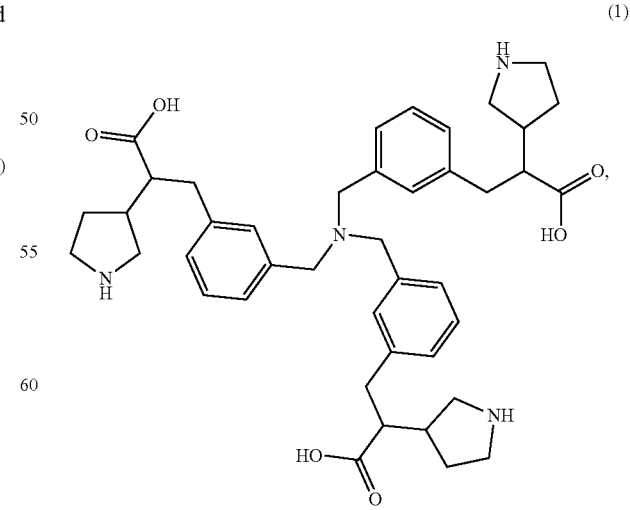

or a pharmaceutically acceptable salt thereof.

An embodiment is a compound of the Formula 2:

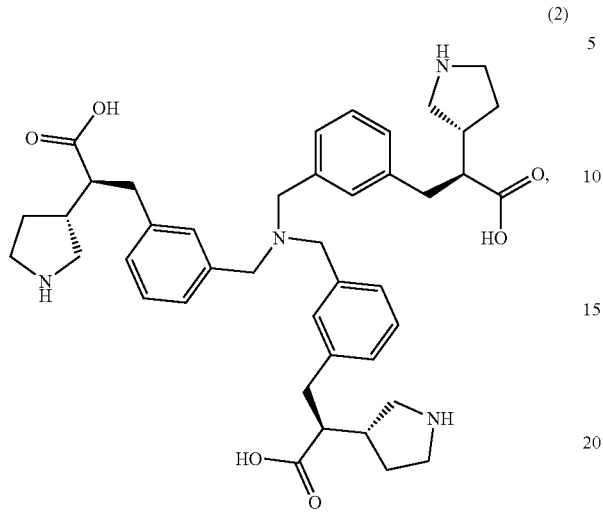

(2)

or a pharmaceutically acceptable salt thereof.

In an embodiment, is a compound of Formula I', I", 1, or Formula 2 wherein the compound is a pharmaceutically acceptable salt. In an embodiment, is a compound of Formula I', Formula 1, or Formula 2 wherein the compound is a hydrochloride salt. In an embodiment, a compound of Formula 1 or Formula 2 wherein the compound is a tetrahydrochloride salt.

In an embodiment, is a compound of Formula I', Formula 1, or Formula 2 wherein the compound is a hydrochloride salt selected from the group consisting of a monohydrochloride, dihydrochloride, trihydrochloride, and tetrahydrochloride. In an embodiment is a compound of Formula 1 or Formula 2 as a zwitter ion.

Provided is a compound of Formula I' wherein L is selected from the group consisting of —CH$_2$NHCH$_2$—, —CH$_2$NH—, —NH—, —S—, —S(O)—, —S(O)$_2$—, —O—, —OCH$_2$—, —OCH$_2$CH$_2$O—, and —NHSO$_2$NH—; or a pharmaceutically acceptable salt thereof.

Provided is a compound of Formula I' wherein R$^1$ and R$^3$ are each H; and L is selected from the group consisting of —CH$_2$NHCH$_2$—, —CH$_2$NH—, —NH—, —S—, —S(O)—, —S(O)$_2$—, —O—, —OCH$_2$—, —OCH$_2$CH$_2$O—, and —NHSO$_2$NH—; or a pharmaceutically acceptable salt thereof.

Provided is a compound of Formula I' wherein R$^1$ and R$^3$ are each H; R$^2$ and R$^4$ are each CH$_3$; and L is selected from the group consisting of —CH$_2$NHCH$_2$—, —CH$_2$NH—, —NH—, —S—, —S(O)—, —S(O)$_2$—, —O—, —OCH$_2$—, —OCH$_2$CH$_2$O—, and —NHSO$_2$NH—; or a pharmaceutically acceptable salt thereof.

Provided is a compound of Formula I' wherein R$^1$ and R$^3$ are each H; R$^2$ and R$^4$ are each H; and L is selected from the group consisting of —CH$_2$NHCH$_2$—, —CH$_2$NH—, —NH—, —S—, —S(O)—, —S(O)$_2$—, —O—, —OCH$_2$—, —OCH$_2$CH$_2$O—, and —NHSO$_2$NH—; or a pharmaceutically acceptable salt thereof.

Provided is a compound of Formula I' wherein L is selected from the group consisting of

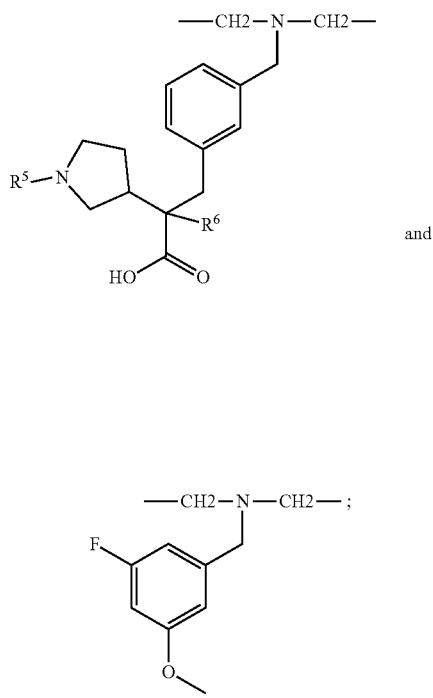

and or a pharmaceutically acceptable salt thereof.

Provided is a compound of Formula I' wherein R$^1$, R$^3$, and R$^5$ are each H; and L is

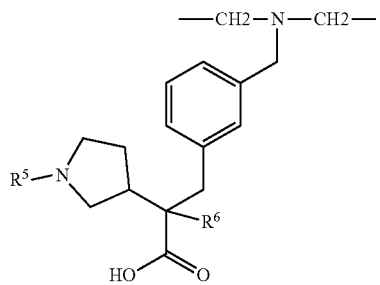

selected from the group consisting of and

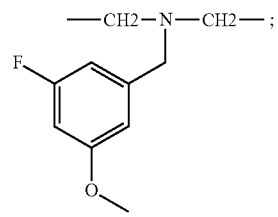

or a pharmaceutically acceptable salt thereof.

Provided is a compound of Formula I' wherein R$^1$, R$^3$, and R$^5$ are each H; R$^2$, R$^4$, and R$^6$ are each H; or a pharmaceutically acceptable salt thereof.

Provided is a compound of Formula I' wherein R$^1$, R$^3$, and R$^5$ are each H; R$^2$, R$^4$, and R$^6$ are each CH$_3$; or a pharmaceutically acceptable salt thereof.

Provided is a compound of Formula I' wherein L is

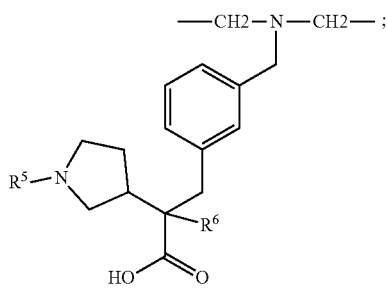

$R^1$, $R^3$, and $R^5$ are each H; $R^2$, $R^4$, and $R^6$ are each $CH_3$; or a pharmaceutically acceptable salt thereof.

In an embodiment is a pharmaceutical composition comprising a compound of Formula I', Formula I", Formula 1, or Formula 2, or a pharmaceutically acceptable salt thereof, and at least one pharmaceutically acceptable carrier, diluent, or excipient.

In an embodiment is a method of treating a patient in need of treatment for cardiovascular disease, comprising administering an effective amount of a compound selected from the group consisting of Formula I', Formula 1, and 2, or a pharmaceutically acceptable salt thereof. In an embodiment is a method of treating a patient in need of treatment for cardiovascular disease, comprising administering an effective amount of a compound of Formula I", or a pharmaceutically acceptable salt thereof. In an embodiment, is a method of treating a patient in need of treatment for elevated Lp(a) plasma levels, comprising administering an effective amount of a compound selected from the group consisting of Formula I', Formula 1, or Formula 2, or a pharmaceutically acceptable salt thereof. In an embodiment, is a method of treating a patient in need of treatment for elevated Lp(a) plasma levels, comprising administering an effective amount of a compound of Formula I", or a pharmaceutically acceptable salt thereof.

In an embodiment, is a compound selected from the group consisting of Formula I, Formula 1, and 2, or a pharmaceutically acceptable salt thereof, for use in therapy. In an embodiment, is a compound of Formula I", or a pharmaceutically acceptable salt thereof, for use in therapy.

In an embodiment, is a compound selected from the group consisting of Formula I, Formula 1, and 2, or a pharmaceutically acceptable salt thereof, for use in the treatment of cardiovascular disease. In an embodiment, is a compound of Formula I", or a pharmaceutically acceptable salt thereof, for use in the treatment of cardiovascular disease.

In an embodiment, is a compound selected from the group consisting of Formula I, Formula 1, and 2, or a pharmaceutically acceptable salt thereof, for use in treating elevated Lp(a) plasma levels.

In an embodiment, is the use of a compound selected from the group consisting of Formula I', Formula 1, and Formula 2, or a pharmaceutically acceptable salt thereof in the manufacture of a medicament of cardiovascular disease.

Lp(a) may exhibit both prothrombotic and antithrombotic properties, and atherothrombotic property. Lp(a) may inhibit fibrinolysis and accumulate in the vascular wall inducing thrombogenesis and atherosclerotic lesions. Plasma levels of Lp(a) vary substantially among individuals. Unlike the other risk factors, Lp(a) plasma levels do not vary significantly with diet and exercise. Lp(a) plasma levels may be linked to genetic predisposition.

Lp(a) resembles LDL-c in that it includes an LDL lipid core with the attendant apolipoprotein B (apoB), but unlike LDL-c, Lp(a) also contains a unique apolipoprotein(a) (apo (a)) bound to the apoB via disulfide bond. Apo(a) is synthesized in the liver. The assembly of Lp(a) from apo(a) and LDL particles can occur in hepatocytes, on the cell wall, or in plasma. Inhibition of the assembly of the LDL particle with apo(a) may reduce Lp(a) levels.

As used herein, the term "elevated Lp(a) plasma levels" means a plasma level that is equal to or above about 50 mg/dL. A compound provided herein may be used in treatment to reduce Lp(a) plasma levels.

The term "pharmaceutically acceptable salt" as used herein refers a salt of a compound that is acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences*, 1977, 66(1), 1-19. The compounds of Formulas I', I", 1 or Formula 2 may be a zwitterion, a mono-, di, or tri-acid addition salt. The compounds of Formulas I', I", 1 or Formula 2 may be a mono-, di, or tri-base addition salt.

The pharmaceutical compositions for the present invention may be prepared using pharmaceutically acceptable additives. The term "pharmaceutically acceptable" refers to one or more carriers, diluents, and/or excipients that are compatible with the other components of the composition and not pharmaceutically deleterious to the patient. Examples of pharmaceutical compositions and processes for their preparation are well known to the skilled artisan, and can be found, for example, in "Remington: The Science and Practice of Pharmacy", Loyd, V., et al. Eds., $22^{nd}$ Ed., Mack Publishing Co., 2012.

As used herein, the term "effective amount" refers to a dosage amount that is effective in treating a disorder. The effective amount for a particular patient can be determined by a skilled health professional.

As used herein, the terms "treating", "to treat", or "treatment", includes slowing, reducing, preventing, or reversing the progression or severity of an existing symptom, disorder, condition, or disease. As used herein, "treating cardiovascular disease" means slowing, reducing, preventing, or reversing the progression of heart or blood vessel disease. Provided is a method to treat myocardial infarction comprising administering a compound of Formula I', Formula 1, or Formula 2 to a patient in need thereof.

As used herein, the term "patient" refers to a mammal. Preferably, the patient is a human.

Pharmaceutical compositions can be formulated as a tablet or capsule for oral administration, a solution for oral administration, or an injectable solution. In an embodiment the composition is suitable for oral administration.

Certain abbreviations are defined as follows: "Apo" refers to Apolipoprotein; "BOC" refers to tert-butoxycarbonyl; "BSA" refers to Bovine Serum Albumin; "DAD" refers to diode array detector; "DCM" refers to dichloromethane or methylene chloride; "de" refers to diasteriomeric excess; "DMEA" refers to dimethylethylamine; "DMEM" refers to Dulbecco's Modified Eagle's Medium; "DMF" refers to N,N-dimethylformamide; "DMSO" refers to dimethyl sulfoxide; "ee" refers to enantiomeric excess; "EACA" refers to epsilon-aminocaproic acid or 6-aminocaproic acid; "ELISA" refers to enzyme-linked immunosorbent assay; "equiv" refers to equivalents; "$Et_2O$" refers to diethyl ether; "EtOAc" refers to ethyl acetate; "EtOH" refers to ethanol or ethyl alcohol; "Ex" refers to example; "FBS" refers to Fetal Bovine Serum; "HEC" refers to hydroxy ethyl cellulose; "HEK" refers to human embryonic kidney; "HepG2" refers to a human hepatoma cell line; "HEPES" refers to 4-(2-hydroxyethyl)-1-piperazineethanesulfonic acid; "HPLC" refers to high-performance liquid chromatography; "HRP" refers to Horseradish Peroxidase; "IC$_{50}$" refers to the concentration of an agent that produces 50% of the maximal inhibitory response possible for that agent; "min" refers to minute or minutes; "MeOH" refers to methanol or methyl alcohol; "MTBE" refers to methyl tert-butyl ether; "RP-HPLC/MS" refers to reverse-phase high performance liquid chromatography with mass spectrometry; "RT" refers to room temperature; "SFC" refers to supercritical fluid chromatography; "SPA" refers to scintillation proximity assay; "t$_{(R)}$" refers to retention time; "THF" refers to tetrahydrofuran; "TMB" refers to 3,3',5,5'-teramethylbenzidine and "Tris" refers to tris(hydroxymethyl)aminomethane.

Individual isomers, enantiomers, and diastereomers may be separated or resolved by one of ordinary skill in the art at any convenient point in the synthesis of compounds listed below, by methods known to the artisan, such as selective crystallization techniques or chiral chromatography.

A compound of Formula I', Formula I", Formula 1, or Formula 2 is readily converted to and may be isolated as a pharmaceutically acceptable salt. Salt formation can occur upon the addition of a pharmaceutically acceptable acid to form the acid addition salt or by the addition of a pharmaceutically acceptable base to form a base addition salt. Salts can also form simultaneously upon deprotection of a nitrogen or oxygen, i.e., removing the protecting group. Examples, reactions and conditions for salt formation are known to the skilled artisan.

The compounds selected from the group consisting of Formula I', Formula I", Formula 1, and Formula 2, or salts thereof, may be prepared by a variety of procedures, some of which are illustrated in the Preparations and Examples below. The specific synthetic steps for each of the routes described may be combined in different ways, or in conjunction with steps from different routes, to prepare compounds or salts of the present invention. The products of each step in the Preparations below can be recovered by conventional methods, including extraction, evaporation, precipitation, chromatography, filtration, trituration, and crystallization.

In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention. Compounds of Formula I', I", Formula 1, and Formula 2, or salts thereof may be prepared by using starting materials or intermediates with the corresponding desired stereochemical configuration.

Scheme 1 depicts the preparation of intermediates which can give access to compounds of the present invention. Protected pyrrolidin-3-yl acetic acid derivative A is first converted to acyl oxazolidinone B. This is accomplished by first converting A to the acid chloride and reacting with (4S)-4-benzyloxazolidin-2-one in the presence of lithium chloride at 10° C. Alkylation of acyl oxazolidinone B with a benzyl bromide derivative and a base such as lithium bis(trimethylsilyl)amide at 0° C. gives intermediate C in a diastereoselective fashion. It is recognized by a person of ordinary skill in the art that the stereochemistry of the oxazolidinone substitution influences the diastereoselectivity of the alkylation, and that use of an oxazolidinone derivative B of opposite or racemic stereochemical configuration in this synthesis could give either the opposite or no diastereoselectivity, respectively. Conversion of acyl oxazolidinone C to the acid intermediate D is accomplished with aqueous LiOH and H$_2$O$_2$ in THF at 5 to 15° C. Acid intermediate D is optionally isolated as an ammonium salt. The acid intermediate D is protected, for example as a tert-butyl ester by reaction with tert-butyl-1,3-diisopropylisourea at elevated temperature to give intermediate E.

Scheme 1 also depicts conversion of acid A to methyl ester F, which is accomplished by reacting A with iodomethane in the presence of a carbonate base. Intermediate F is then alkylated with a benzyl bromide derivative using a base such as lithium bis(trimethylsilyl)amide at −78° C. to give intermediate G. Intermediate G is alkylated again with iodomethane using a base such as lithium bis(trimethylsilyl) amide at −78° C., and the ester is then hydrolyzed with sodium hydroxide at elevated temperature to give acid intermediate H. The acid intermediate H is protected, for example as a tert-butyl ester by reaction with tert-butyl-1, 3-diisopropylisourea at elevated temperature to give intermediate I.

In particular, intermediates D, E, H, and I where Ra is bromine or —NO$_2$ are particularly useful for further transformations in the preparation of compounds of Formula I'. Intermediate D where Ra is —H can be prepared either by alkylation of B with benzyl bromide followed by hydrolysis of the acyl oxazolidinone, or by stirring intermediate D where Ra is bromine with palladium on carbon under a hydrogen atmosphere. When Ra is —H, deprotected of the pyrrolidine nitrogen on intermediate D gives compounds of formula I".

Scheme 1

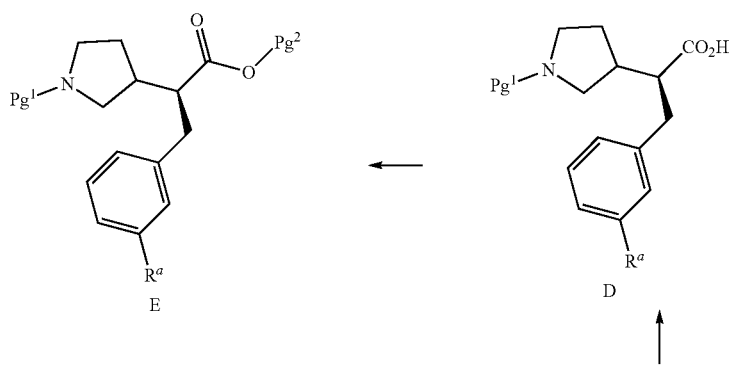

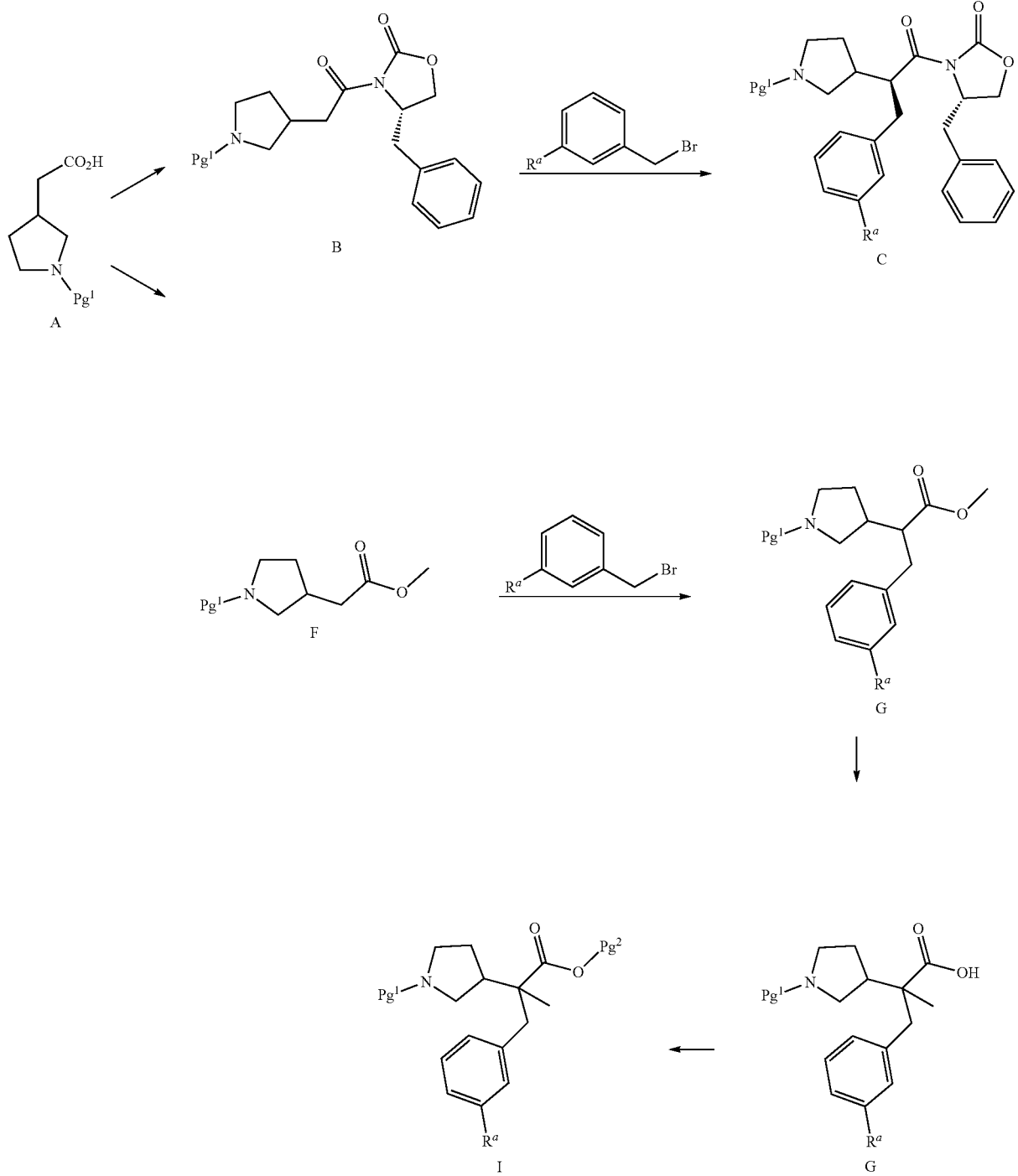

$R^a$ = H, Br, $NO_2$
Pg = protecting group

Scheme 2 depicts the conversion of a key intermediate (J, prepared as described in Scheme 1) into penultimate compounds of the present invention. The bromide is converted to the aldehyde K using syngas (1:1 $CO/H_2$), palladium(II) acetate, butyldi-1-adamantylphosphine, and N,N,N',N'-tetramethylethylenediamine at an elevated temperature. Aldehyde K is then converted to a mixture of N and O by reductive amination of K (2 or 3 equivalents, respectively) with ammonia and a reducing agent such as sodium triacetoxyborohydride or sodium cyanoborohydride, and then N and O are separated by chromatography. Alternatively, dimeric compound O is prepared by converting aldehyde K to aldoxime L, reducing L to the amine M by flow hydrogenation using a sponge nickel catalyst at elevated temperature, and then reductive amination of amine M with aldehyde K. Intermediate P is prepared by reductive amination of dimeric intermediate O with 3-fluoro-5-methoxybenzaldehyde.

Scheme 2

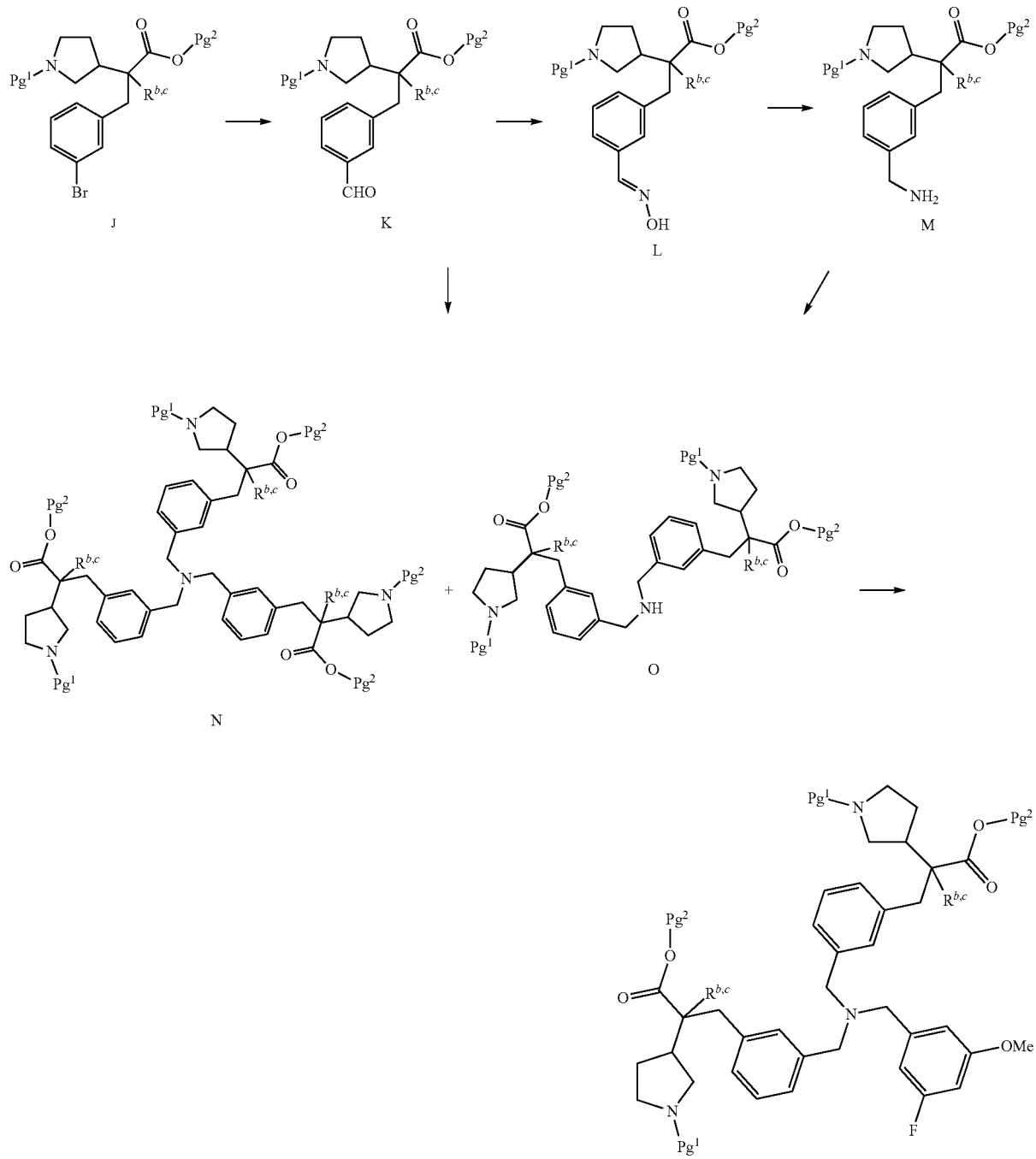

$R^b$ and $R^c$ independently = —H or —CH$_3$

Scheme 3 shows further use of bromide intermediate J to prepare penultimate compounds of the present invention. Bromide J is converted to boronic acid Q using tetrahydroxydiboron, chloro(2-dicyclohexylphosphino-2',4',6'-tri-i-propyl-1,1'-biphenyl)(2'-amino-1,1'-biphenyl-2-yl) palladium(II), X-PHOS, and potassium acetate at an elevated temperature. Boronic acid Q is then converted to phenol T using H$_2$O$_2$ at 5° C. Phenol T is coupled onto bromide J using copper(I) iodide, N,N-dimethylglycine hydrochloride, and cesium carbonate at an elevated temperature to give biphenyl ether U. Phenol T is also reacted with 1,2-dibromoethane and a carbonate base at an elevated temperature to give V. Aldehyde intermediate K (prepared from bromide J as described in Scheme 2) is reduced with sodium borohydride at 0° C. to alcohol R, which then undergoes a Mitsunobu reaction to give intermediate S.

Scheme 3

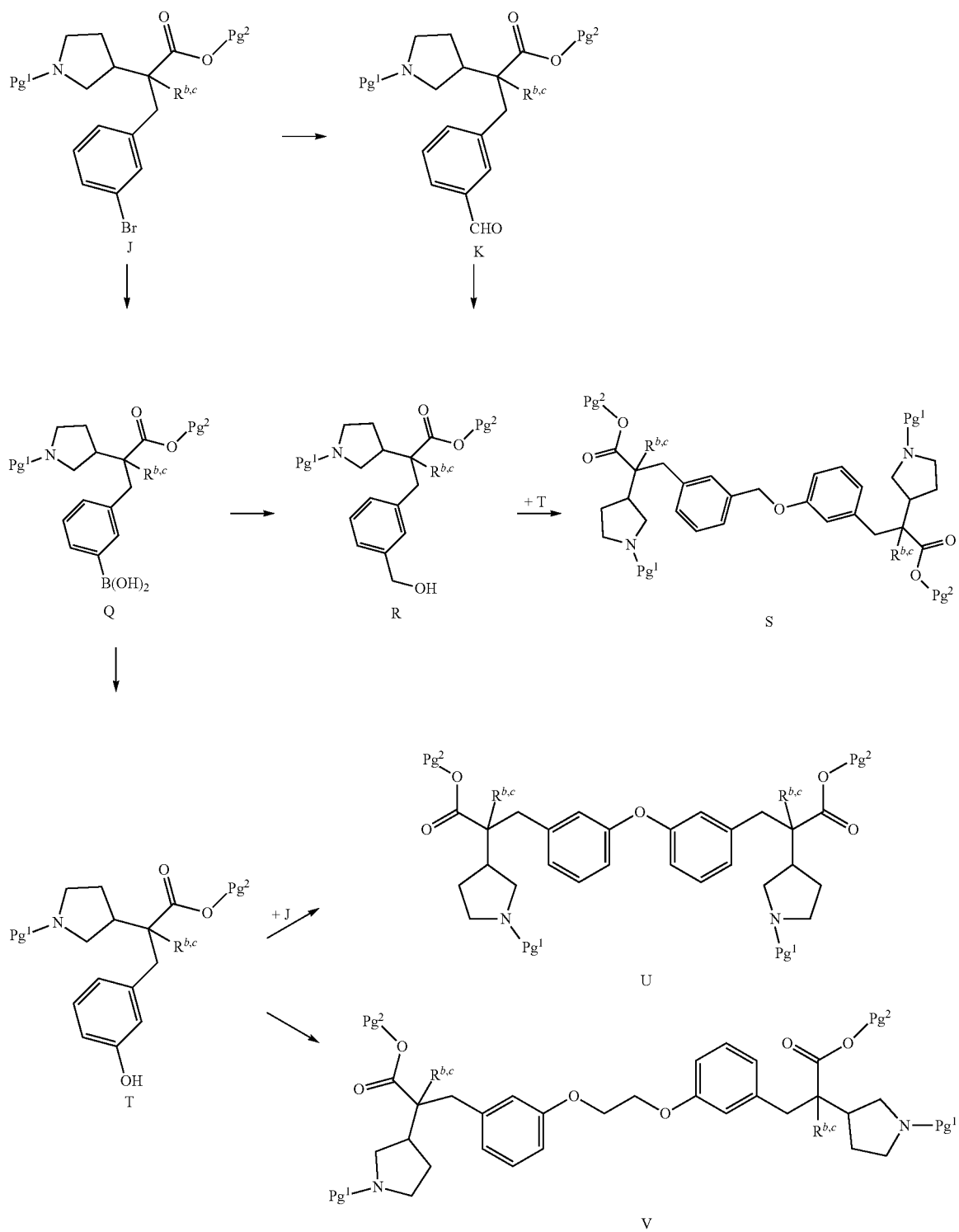

$R^b$ and $R^c$ independently = —H or —CH$_3$

Scheme 4 shows further use of bromide intermediate J to prepare penultimate compounds of the present invention. Two equivalents of bromide J are coupled with potassium thioacetate using bis(dibenzylideneacetone)palladium, potassium phosphate tribasic), 1,1'-bis(diphenylphosphino) ferrocene to give the diphenyl sulfide W. Sulfide W is then converted to either the sulfone X or sulfoxide Y using either 1 or 2 equivalents of meta-chloroperoxybenzoic acid, respectively.

Scheme 4

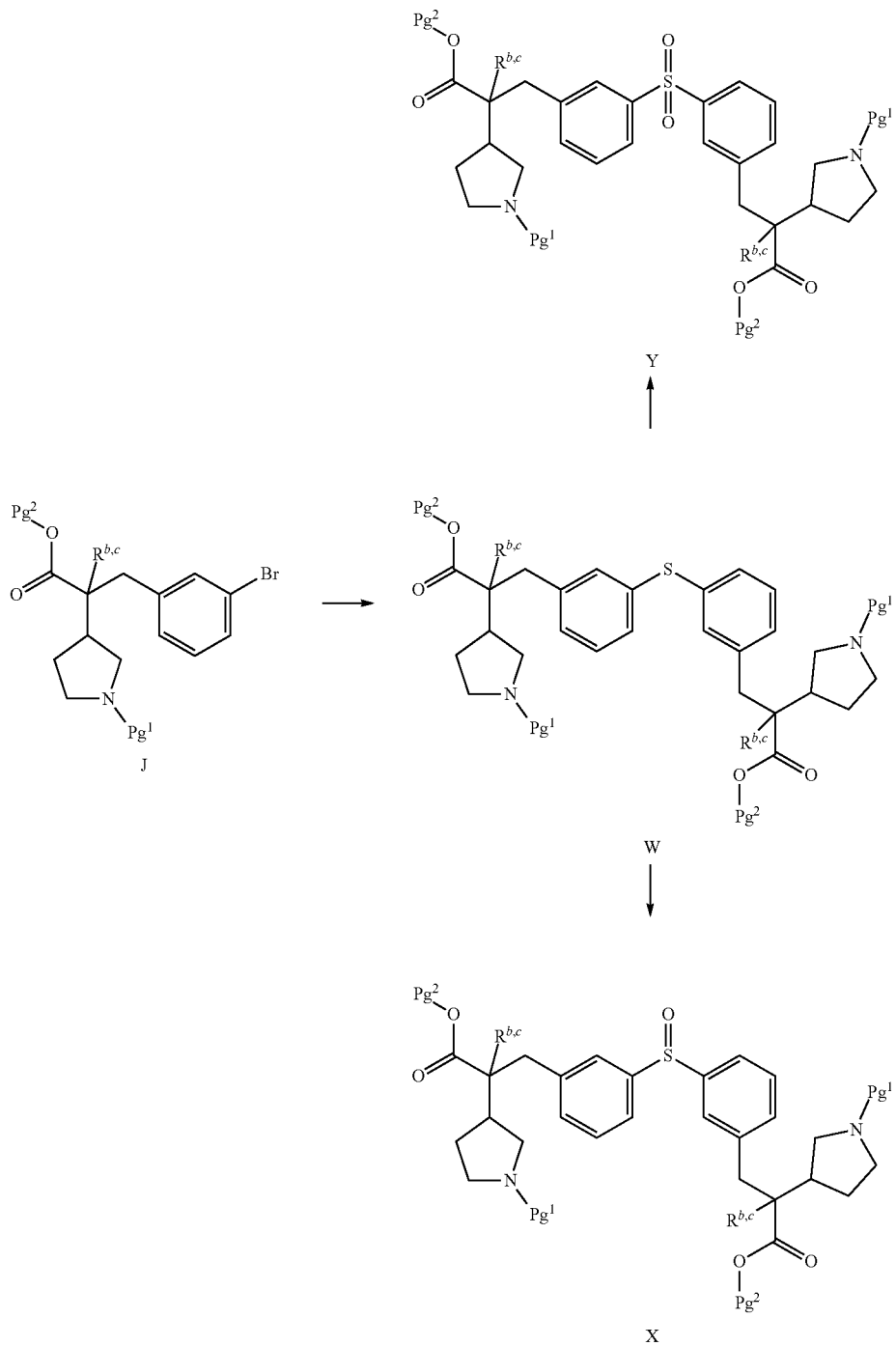

$R^b$ and $R^c$ independently = —H or —CH$_3$

Scheme 5 depicts use of nitro intermediate Z (prepared as in Scheme 1) to prepare penultimate compounds of the present invention. Nitro intermediate Z is reduced to aniline AA in the presence of a catalyst under hydrogen atmosphere. Aniline AA undergoes reductive amination with aldehyde K (prepared as in Scheme 2) using a reducing agent such as sodium triacetoxyborohydride to give CC. Buchwald reaction between aniline AA and bromide BB (prepared as in Scheme 1) using [(2-di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3) and potassium carbonate at elevated temperature gives diphenylamine derivative DD. Two equivalents of aniline AA are also reacted with 1,4-diazabicyclo[2.2.2]octane bis (sulfur dioxide) adduct (DABSO) and iodine at elevated temperature to give sulfamide EE.

Scheme 5

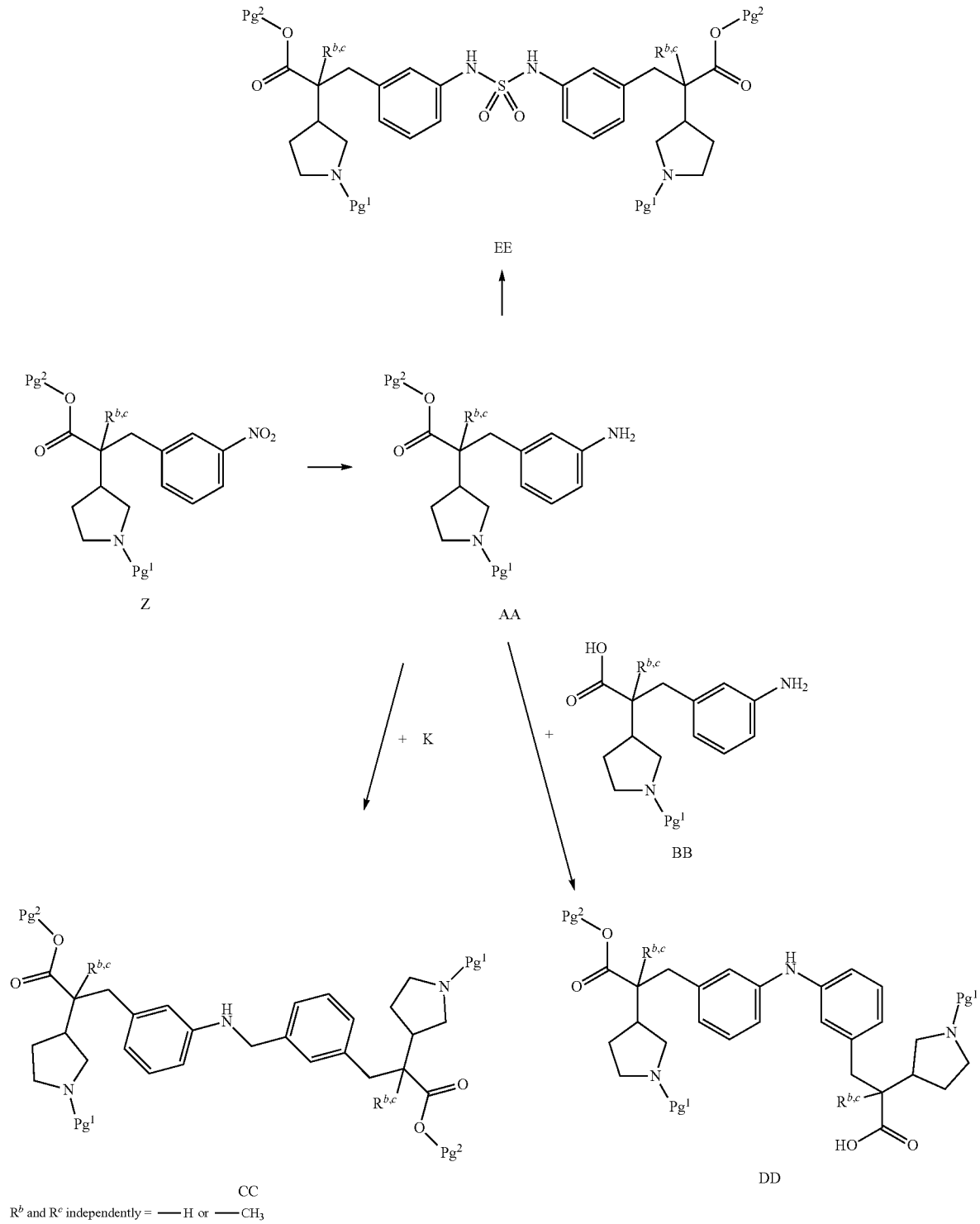

Global deprotection of intermediates N, O, P, S, U, V, W, X, Y, CC, DD, and EE from Schemes 2 through 5 give compounds of Formula I'. If the pyrrolidine protecting group ($Pg^1$ in Schemes 1 through 5) is —BOC and the ester ($Pg^2$ in Schemes 1 through 5) is a tert-butyl ester, global deprotection is accomplished in one step using a solution of HCl in an organic solvent such as diethyl ether, dioxane, or isopropanol. Upon deprotection, the pyrrolidine nitrogen in compounds of Formula I' can be methylated by reductive amination with paraformaldehyde and sodium triacetoxyborohydride.

Preparation 1 tert-Butyl (3R)-3-[2-[(4S)-4-benzyl-2-oxo-oxazolidin-3-yl]-2-oxo-ethyl]pyrrolidine-1-carboxylate

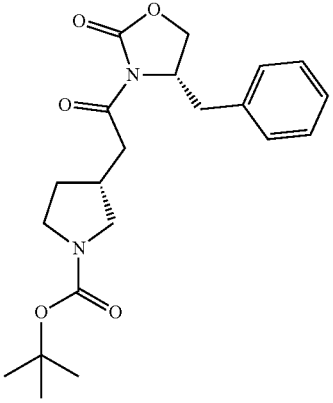 [SMILES: CC(C)(C)OC(=O)N1CC[C@H](CC(=O)N2C(=O)OC[C@@H]2Cc2ccccc2)C1]

Add triethylamine (56.5 g, 77.9 mL, 559 mmol, 2.5 equiv) to a solution of 2-[(3R)-1-tert-butoxycarbonylpyrrolidin-3-yl]acetic acid (53.8 g, 235 mmol, 1.05 equiv) in THF (540 mL) maintained at 10° C. After 5 min, add pivaloyl chloride (33.7 g, 34.2 mL, 279 mmol, 1.25 equiv). After 15 min, add lithium chloride (11.8 g, 279 mmol, 1.25 equiv) in THF (540 mL) and (4S)-4-benzyloxazolidin-2-one (40.0 g, 223 mmol, 1 equiv). Allow the mixture to warm to RT and stir 24 h. After 24 h, add 1N aqueous HCl (500 mL) and separate the organic phase from the aqueous phase. Wash the organic phase with 1N aqueous NaOH (500 mL) and saturated aqueous NaCl (500 mL), dry over MgSO$_4$, filter, and concentrate the solution in-vacuo. Suspend the residue in a mixture of MeOH/water (1:2, 575 mL) and stir at RT overnight. Filter off the solid, wash with hexanes (2×150 mL), and dry the solid to give the title compound (65.7 g, 76%). ES/MS (m/z): 333 (M+H-tert-butyl), $^1$H NMR (400.13 MHz, CDCl$_3$) δ 7.38-7.28 (m, 3H), 7.25-7.20 (m, 2H), 4.73-4.70 (m, 1H), 4.27-4.19 (m, 2H), 3.75-3.66 (m, 1H), 3.55-3.48 (m, 1H), 3.38-3.30 (m, 2H), 3.11-2.96 (m, 3H), 2.84-2.76 (m, 1H), 2.74-2.65 (m, 1H), 2.14-2.11 (m, 1H), 1.64-1.58 (m, 1H), 1.49 (s, 9H).

Preparation 2 tert-Butyl (3S)-3-[2-[(4R)-4-benzyl-2-oxo-oxazolidin-3-yl]-2-oxo-ethyl]pyrrolidine-1-carboxylate

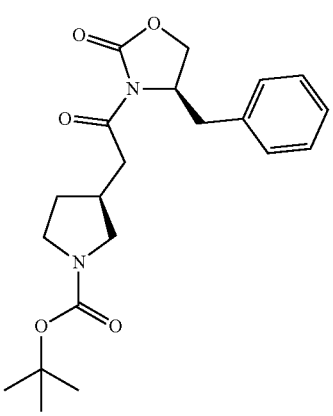 [SMILES: CC(C)(C)OC(=O)N1CC[C@@H](CC(=O)N2C(=O)OC[C@H]2Cc2ccccc2)C1]

Prepare the title compound essentially as described in Preparation 1 using 2-[(3S)-1-tert-butoxycarbonylpyrrolidin-3-yl]acetic acid and (4R)-4-benzyloxazolidin-2-one. Purify the product by silica gel chromatography using a gradient of 10 to 50% EtOAc in hexanes. ES/MS (m/z): 333 (M+H-tert-butyl)

Preparation 3 tert-Butyl (3R)-3-(2-methoxy-2-oxo-ethyl)pyrrolidine-1-carboxylate

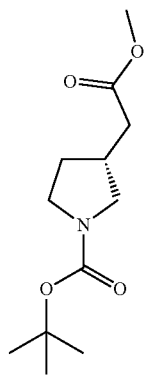 [SMILES: COC(=O)C[C@H]1CCN(C(=O)OC(C)(C)C)C1]

Add iodomethane (2 mol/L in MTBE, 240 mL, 480 mmol, 1.1 equiv) to a solution of 2-[(3R)-1-tert-butoxycarbonylpyrrolidin-3-yl]acetic acid (100 g, 436 mmol) in DMF (800 mL) at RT. Add potassium carbonate (90.4 g, 654 mmol, 1.5 equiv) and stir the resulting mixture for 4 h. Add water (1.5 L) and extract with MTBE (3 L). Wash the organic phase with ice/water (3×500 mL), dry the organic phase over MgSO$_4$, filter and concentrate the solution under reduced pressure to give the title compound (103 g, 97%). $^1$H NMR (300 MHz, CDCl3) δ 3.68 (s, 3H), 3.65-3.53 (m, 1H), 3.52-3.36 (m, 1H), 3.35-3.23 (m, 1H), 3.03-2.84 (m, 1H), 2.64-2.49 (m, 1H), 2.45-2.30 (m, 2H), 2.13-1.97 (m, 1H), 1.65-1.48 (m, 1H), 1.45 (s, 9H).

Preparation 4 tert-Butyl (3R)-3-[1-[(3-bromophenyl)methyl]-2-methoxy-2-oxo-ethyl]pyrrolidine-1-carboxylate

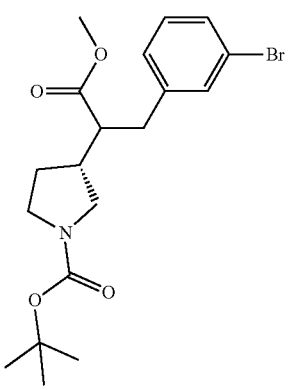 [SMILES: COC(=O)C(Cc1cccc(Br)c1)[C@H]1CCN(C(=O)OC(C)(C)C)C1]

To a solution of tert-butyl (3R)-3-(2-methoxy-2-oxo-ethyl)pyrrolidine-1-carboxylate (7 g, 28 mmol) in THF (93 mL) at −78° C., add lithium bis(trimethylsilyl)amide (1 M solution in THF, 33.5 mL, 33.5 mmol, 1.2 equiv). Stir the mixture at −78° C. for 1 h. Add a solution of 3-bromobenzyl bromide (8.37 g, 33.5 mmol, 1.2 equiv) in THF (5 mL). Allow the mixture to warm up to RT and stir overnight. Quench the mixture with saturated aqueous NH₄Cl and extract with EtOAc. Wash the organics with saturated aqueous NaCl, dry over MgSO₄, filter and evaporate to dryness. Purify the residue by silica gel chromatography using a gradient of 10 to 40% EtOAc in hexanes to give a mixture of diastereomers of the title compound (8.4 g, 73%) as a yellow oil. ES/MS (m/z): 356, 358 (M+H-tert-butyl).

Preparation 5

3-(3-Bromophenyl)-2-[(3R)-1-tert-butoxycarbo-nylpyrrolidin-3-yl]-2-methyl-propanoic acid

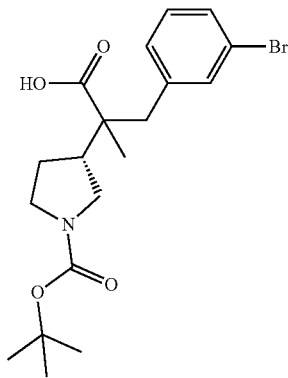 [SMILES: CC(C)(C)OC(=O)N1CC[C@H](C(C)(Cc2cccc(Br)c2)C(=O)O)C1]

To a solution of tert-butyl (3R)-3-[1-[(3-bromophenyl) methyl]-2-methoxy-2-oxo-ethyl]pyrrolidine-1-carboxylate (8.4 g, 20 mmol) in THF (100 mL) under nitrogen and at −78° C., add lithium bis(trimethylsilyl)amide (1 M solution in THF, 41 mL, 41 mmol, 2 equiv). Stir the reaction at −78° C. for 2 h. Add iodomethane (25 mL, 410 mmol, 20 equiv) and allow the mixture to warm up to RT. Stir the mixture overnight. Add saturated aqueous NH₄Cl and extract with EtOAc. Wash the organic layer with saturated aqueous NaCl and dry over MgSO₄, filter and remove the solvent in-vacuo. Dissolve the residue in MeOH (80 mL) and THF (80 mL), then add sodium hydroxide (5 M solution in water, 81 mL, 410 mmol, 20 equiv) and heat the resulting mixture at 60° C. for 3 days. Allow the mixture to cool down to RT, add HCl (1 N aqueous solution) to adjust the mixture pH to 2-3. Extract the aqueous layer with EtOAc. Dry the organic layer over MgSO₄, filter and concentrate in-vacuo. Subject the residue to chiral SFC under the following parameters: column—Chiralpak® AD (25×3 cm, 5 μm); mobile phase—solvent A=CO₂, solvent B=MeOH+0.2% v/v DMEA; gradient—isocratic 80:20 A:B; flow rate—120 mL/min). Obtain isomer 1 (1.7 g, 27%) and isomer 2 (3.4 g, 41%) of the title compound as white solids. ES/MS (m/z): 356/358 (M+H-tert-butyl).

Preparation 6 tert-Butyl (3R)-3-[(1S)-2-[(4S)-4-benzyl-2-oxo-oxazolidin-3-yl]-1-[(3-bromophenyl)methyl]-2-oxo-ethyl]pyrrolidine-1-carboxylate

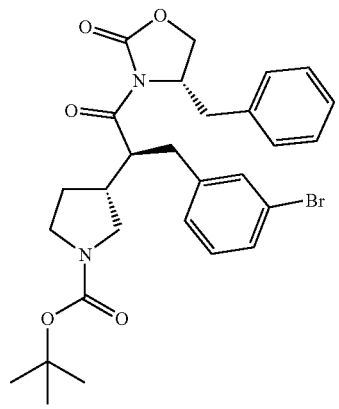 [SMILES: CC(C)(C)OC(=O)N1CC[C@H]([C@H](Cc2cccc(Br)c2)C(=O)N2C(=O)OC[C@@H]2Cc2ccccc2)C1]

Add a solution of lithium bis(trimethylsilyl)amide (1M in THF, 818 mL, 818 mmol, 1.2 equiv) over 29 min to a 0° C. solution of tert-butyl (3R)-3-[2-[(4S)-4-benzyl-2-oxo-oxazolidin-3-yl]-2-oxo-ethyl]pyrrolidine-1-carboxylate (265 g, 682 mmol) in THF (1325 mL) in a 3-neck 3 L round-bottom flask in an ice bath under nitrogen with mechanical stirring. Stir the mixture for 47 min at 0.6° C. Then add a solution of 1-bromo-3-(bromomethyl)benzene (190 g, 760 mmol, 1.12 equiv) in THF (450 mL) over 28 min, raising the reaction temperature to 5.1° C. Allow the mixture to warm up to RT with stirring overnight. Cool the reaction mixture using an ice/water bath, then add a saturated aqueous solution of NH₄Cl (1 L) in 4 portions at such a rate as to maintain the reaction temperature below 21° C. Add water (1 L) to the mixture and extract with MTBE (3.5 L). Wash the organic layer with a mixture of water (1 L) and saturated aqueous NaCl (500 mL), then with saturated aqueous NaCl (500 mL). Dry the organics over Na₂SO₄, filter, then concentrate in-vacuo. To the residue add hexanes (1 L) and concentrate in-vacuo, then dry under high vacuum overnight to obtain the title compound as an orange oil (416 g, >100%), purity estimated at 90 wt % based on theoretical yield. ES/MS (m/z): 501/503 (M+H-tert-butyl).

Preparation 7 tert-Butyl (3S)-3-[(1R)-2-[(4R)-4-benzyl-2-oxo-oxazolidin-3-yl]-1-[(3-bromophenyl)methyl]-2-oxo-ethyl]pyrrolidine-1-carboxylate

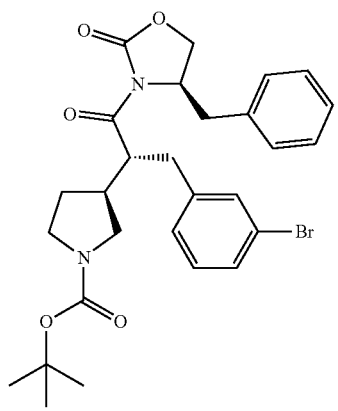 [SMILES: CC(C)(C)OC(=O)N1CC[C@@H]([C@@H](Cc2cccc(Br)c2)C(=O)N2C(=O)OC[C@H]2Cc2ccccc2)C1]

Prepare the title compound essentially as described for Preparation 6 using tert-butyl (3S)-3-[2-[(4R)-4-benzyl-2-oxo-oxazolidin-3-yl]-2-oxo-ethyl]pyrrolidine-1-carboxylate. ES/MS (m/z): 501, 503 (M+H-tert-butyl).

Preparation 8 tert-Butyl (3R)-3-[(1S)-2-[(4S)-4-benzyl-2-oxo-oxazolidin-3-yl]-1-[(3-nitrophenyl)methyl]-2-oxo-ethyl]pyrrolidine-1-carboxylate

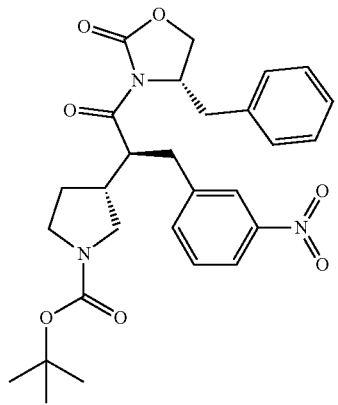 [SMILES: CC(C)(C)OC(=O)N1CC[C@H]([C@H](Cc2cccc([N+](=O)[O-])c2)C(=O)N2C(=O)OC[C@@H]2Cc2ccccc2)C1]

Add lithium bis(timethylsilyl)amide (1.0 M in THF, 46 mL, 46 mmol, 1.2 equiv) to a solution of tert-butyl (3R)-3-[2-[(4S)-4-benzyl-2-oxo-oxazolidin-3-yl]-2-oxo-ethyl]pyrrolidine-1-carboxylate (15 g, 39 mmol, 1 equiv) in THF (75 mL) at −20° C. Stir the mixture at −20° C. for 20 min. Add a solution of 1-(bromomethyl)-3-nitro-benzene (9.17 g, 42.5 mmol, 1.1 equiv) in THF (45 mL). Stir the solution for 2 h and allow it to warm up to RT. Dilute the mixture with MTBE and quench with a saturated aqueous solution of NH4Cl. Separate the phases and extract the aqueous phase with MTBE. Combine the organic extracts and wash the organics sequentially with water and saturated aqueous NaCl. Dry over Na2SO4, filter, and concentrate the filtrate in-vacuo. Triturate the residue with a mixture of MeOH/H2O (2:1, 150 mL). Stir the slurry overnight. Filter to collect the solid and wash with hexanes. Dry the solid in-vacuo at 40° C. to give the title compound (19 g, 88%). ES/MS (m/z): 468 (M+H-tert-butyl).

Preparation 9 tert-Butyl (3R)-3-[(1S)-1-benzyl-2-[(4S)-4-benzyl-2-oxo-oxazolidin-3-yl]-2-oxo-ethyl]pyrrolidine-1-carboxylate

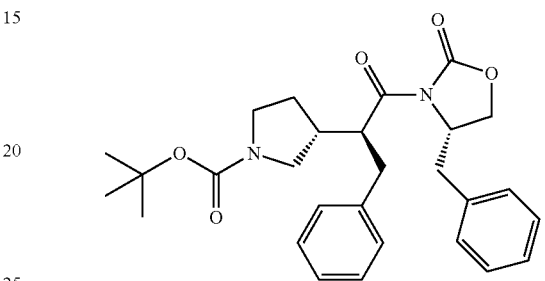

Prepare the title compound in 76% purity essentially as described in Preparation 6 using benzyl bromide. ES/MS (m/z): 423 (M+H-tert-butyl).

Preparation 10

(2S)-3-(3-Bromophenyl)-2-[(3R)-1-tert-butoxycarbonylpyrrolidin-3-yl]propanoic acid

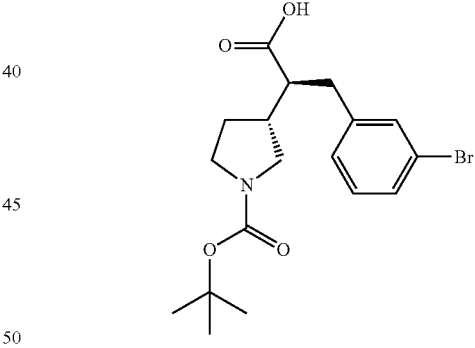

Add a solution of hydrogen peroxide (0.88 M in water, 105 mL, 926 mmol, 1.5 equiv) in one portion to a mechanically-stirred mixture of tert-butyl (3R)-3-[(1S)-2-[(4S)-4-benzyl-2-oxo-oxazolidin-3-yl]-1-[(3-bromophenyl)methyl]-2-oxo-ethyl]pyrrolidine-1-carboxylate (90 wt % pure, 381 g, 615 mmol) in THF (4 L) and cool to 8.6° C. in a 3-neck 12 L round-bottom flask with an ice/water bath. Add a solution of lithium hydroxide monohydrate (38.7 g, 923 mmol, 1.5 equiv) in water (930 mL) over 25 min. raising the reaction temperature to 12.8° C. Stir the reaction for 2.5 h then cool to 5.7° C. Add a solution of sodium bisulfite (129.4 g, 1244 mmol, 2.02 equiv) in water (2 L) over 40 min, raising the reaction temperature to 14.7° C. Add an aqueous solution of NaOH (5N) to raise the pH of the reaction mixture to >12, then add water (1 L) and MTBE (4 L). Separate the layers and extract the aqueous layer with MTBE (2 L). Combine the organics, extract with water (1 L), then add this aqueous extraction to the bulk aqueous solution. Stir the aqueous solution with MTBE (3 L) and cool the mixture to 5° C. Add an aqueous solution of hydrochloric acid (5N) to bring the pH of the mixture to 3. Separate the layers and wash the organic layer with a mixture of saturated aqueous NaCl (1 L) and water (500 mL). Dry the organics over Na₂SO₄, filter, and concentrate in-vacuo at 40° C. Dry the residue under high-vacuum to obtain the title compound (221.5 g, 90%) as a white solid. ES/MS (m/z): 342/344 (M+H-tert-butyl).

Preparation 11

Ammonium; (2S)-3-(3-bromophenyl)-2-[(3R)-1-tert-butoxycarbonylpyrrolidin-3-yl]propanoate

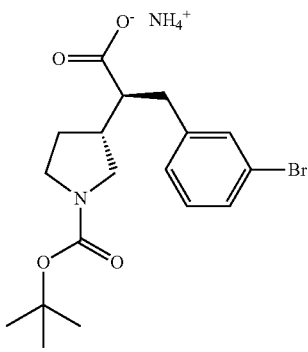 [SMILES: [NH4+] ; CC(C)(C)OC(=O)N1CC[C@H]([C@H](Cc2cccc(Br)c2)C(=O)[O-])C1]

Mix (2S)-3-(3-bromophenyl)-2-[(3R)-1-tert-butoxycarbonylpyrrolidin-3-yl]propanoic acid (237.6 g, 596.5 mmol) and MTBE (3801 mL) to give a cloudy mixture with solids. Filter the mixture over 2 glass fiber filter papers, and add ammonia (7 M) in MeOH (128 mL, 896 mmol, 1.5 equiv) to the filtrate under nitrogen with mechanical stirring. A white solid precipitates and the mixture becomes very thick. Add MTBE (800 mL) to the mixture to give a free-flowing slurry. Stir the mixture at RT for 1.5 h, then cool −5 to 0° C. in an ice/acetone bath and stir for 1.5 h. Filter the solid by vacuum filtration through a propylene mat and a 3 L glass-fritted funnel and rinse the solid with MTBE (1 L), then continue applying vacuum at RT overnight under a blanket of nitrogen. Combine the solid with two more batches of material prepared in a similar manner starting with (2S)-3-(3-bromophenyl)-2-[(3R)-1-tert-butoxycarbonylpyrrolidin-3-yl]propanoic acid (47.3 g, 113 mmol, and 53.0 g, 120 mmol). Suspend the solid in acetonitrile (4300 mL) and stir the mixture at 23° C. with mechanical stirring under nitrogen overnight. Filter the solid by vacuum filtration and wash with acetonitrile (500 mL) and MTBE (1 L), then continue applying vacuum for 4 h at RT under a blanket of nitrogen to obtain the title compound as a white powder (249.5 g, 77%). ES/MS (m/z): 342/344 (M+H-tert-butyl).

Preparation 12

Ammonium; (2R)-3-(3-bromophenyl)-2-[(3S)-1-tert-butoxycarbonylpyrrolidin-3-yl]propanoate

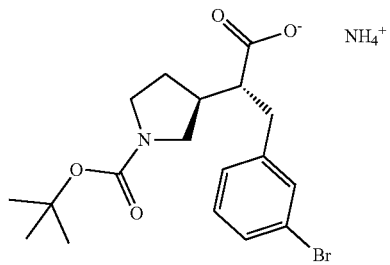 [SMILES: CC(C)(C)OC(=O)N1CC[C@@H]([C@@H](Cc2cccc(Br)c2)C(=O)[O-])C1 ; [NH4+]]

Prepare the title compound essentially as described in Preparation 10 using tert-butyl (3S)-3-[(1R)-2-[(4R)-4-benzyl-2-oxo-oxazolidin-3-yl]-1-[(3-bromophenyl)methyl]-2-oxo-ethyl]pyrrolidine-1-carboxylate, followed by ammonium salt formation as described in Preparation 11. ES/MS (m/z): 342, 344 (M+H-tert-butyl).

Preparation 13

(2S)-2-[(3R)-1-tert-Butoxycarbonylpyrrolidin-3-yl]-3-(3-nitrophenyl)propanoic acid

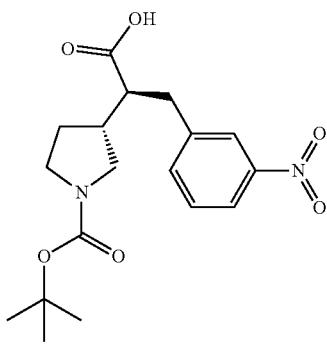 [SMILES: CC(C)(C)OC(=O)N1CC[C@H]([C@H](Cc2cccc([N+](=O)[O-])c2)C(=O)O)C1]

Prepare the title compound essentially as described in Preparation 10 using tert-butyl (3R)-3-[(1S)-2-[(4S)-4-benzyl-2-oxo-oxazolidin-3-yl]-1-[(3-nitrophenyl)methyl]-2-oxo-ethyl]pyrrolidine-1-carboxylate, omitting the step of adding an aqueous solution of sodium bisulfite in the reaction workup. ES/MS (m/z): 309 (M+H-tert butyl).

Preparation 14

(2S)-2-[(3R)-1-tert-Butoxycarbonylpyrrolidin-3-yl]-3-phenyl-propanoic acid

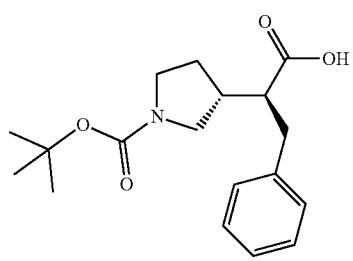 [SMILES: CC(C)(C)OC(=O)N1CC[C@H]([C@H](Cc2ccccc2)C(=O)O)C1]

Prepare the title compound essentially as described in Preparation 10 using tert-butyl (3R)-3-[(1S)-1-benzyl-2-[(4S)-4-benzyl-2-oxo-oxazolidin-3-yl]-2-oxo-ethyl]pyrrolidine-1-carboxylate. Purify the product by trituration with 1:1 MeOH:water. ES/MS (m/z): 264 (M+H-tert butyl).

Preparation 15

(2R)-2-[(3S)-1-tert-Butoxycarbonylpyrrolidin-3-yl]-3-phenyl-propanoic acid

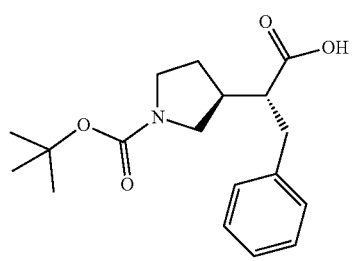 [SMILES: CC(C)(C)OC(=O)N1CC[C@@H]([C@@H](Cc2ccccc2)C(=O)O)C1]

Dissolve ammonium; (2R)-3-(3-bromophenyl)-2-[(3S)-1-tert-butoxycarbonylpyrrolidin-3-yl]propanoate (830 mg, 2.08 mmol) in EtOH (20 mL) and add palladium on carbon (10% w/w, 222 mg, 0.208 mmol, 0.1 equiv). Stir the mixture under a balloon of hydrogen at RT overnight. Filter the reaction mixture over a pad of diatomaceous earth. Concentrate the filtrate and purify the residue by silica gel chromatography using a gradient of 10 to 40% EtOAc in hexanes with an addition of 1% acetic acid to give the title compound (560 mg, 84%) as a white solid. ES/MS (m/z): 264 (M+H-tert-butyl).

Preparation 16 tert-Butyl (3R)-3-[(1S)-1-[(3-bromophenyl)methyl]-2-tert-butoxy-2-oxo-ethyl]pyrrolidine-1-carboxylate

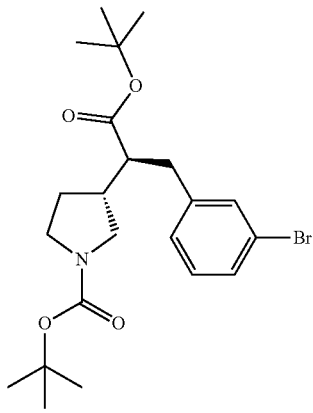 [SMILES: CC(C)(C)OC(=O)[C@@H](Cc1cccc(Br)c1)[C@H]1CCN(C(=O)OC(C)(C)C)C1]

Add to a reactor ammonium; (2S)-3-(3-bromophenyl)-2-[(3R)-1-tert-butoxycarbonylpyrrolidin-3-yl]propanoate (500 g, 1210 mmol), 2-methyltetrahydrofuran (4000 mL), and then a solution of KHSO$_4$ (1M in water, 3000 mL). Stir the mixture for min, during which time the pH is measured to be 2-3. Separate the phases of the reaction mixture and extract the aqueous layer with 2-methyltetrahydrofuran (1000 mL). Combine the organic phases and wash them with saturated aqueous NaCl. Dry the organic phase over MgSO$_4$ and filter it. Transfer the solution to a reactor and add 2-tert-butyl-1,3-diisopropylisourea (618.2 g, 3024 mmol, 2.5 equiv). Stir the mixture at 65° C. for three hours and add more 2-tert-butyl-1,3-diisopropylisourea (247.3 g, 1210 mmol, 1 equiv). Stir the mixture at 65° C. overnight. Cool the mixture to RT. Filter off the solid and wash the organic layer with saturated aqueous NaHCO$_3$ (1000 mL). Dry the organic layer over MgSO$_4$, filter and concentrate in-vacuo. Add MTBE (2000 mL) to the residue and filter off the solid. Concentrate the filtrate to obtain the title compound (483 g, 88%) as a white solid. ES/MS (m/z): 342/344 (M+H–2× tert-butyl)

Preparation 17 tert-Butyl (3R)-3-[1-[(3-bromophenyl)methyl]-2-tert-butoxy-1-methyl-2-oxo-ethyl]pyrrolidine-1-carboxylate

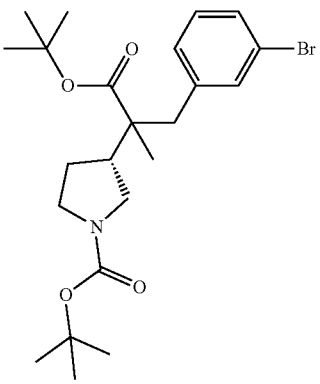 [SMILES: CC(C)(C)OC(=O)N1CC[C@H](C(C)(Cc2cccc(Br)c2)C(=O)OC(C)(C)C)C1]

To a solution of 3-(3-bromophenyl)-2-[(3R)-1-tert-butoxycarbonylpyrrolidin-3-yl]-2-methyl-propanoic acid, isomer 2 (3.4 g, 8.2 mmol) in 2-methyltetrahydrofuran (33 mL) add 2-tert-butyl-1,3-diisopropylisourea (5.1 g, 5.7 mL, 25 mmol, 3 equiv) and heat the mixture at 55° C. for 3.5 h. Add additional 2-tert-butyl-1,3-diisopropylisourea (5.1 g, 5.7 mL, 25 mmol, 3 equiv) and continue heating the reaction at 55° C. for 1.5 h. Add additional 2-tert-butyl-1,3-diisopropylisourea (2.5 g, 2.9 mL, 12 mmol, 1.5 equiv) and continue heating the reaction at 55° C. overnight. Filter off a white solid and wash with MTBE, then evaporate the filtrate to dryness. Purify the residue by silica gel chromatography using a gradient of 0 to 100% EtOAc in hexanes to give the title compound (3.6 g, 93%) as a yellow oil. ES/MS (m/z): 356, 358 [M+H− (2×tert-butyl)].

Preparation 18 tert-Butyl (3R)-3-[(1S)-2-tert-butoxy-1-[(3-nitrophenyl)methyl]-2-oxo-ethyl]pyrrolidine-1-carboxylate

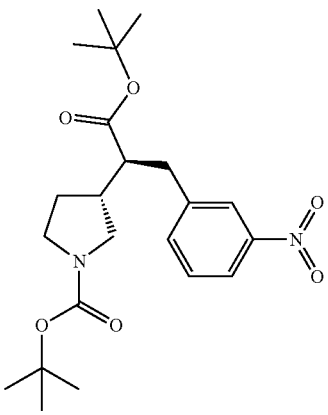 [SMILES: CC(C)(C)OC(=O)[C@@H](Cc1cccc([N+](=O)[O-])c1)[C@H]1CCN(C(=O)OC(C)(C)C)C1]

Prepare the title compound essentially as described in Preparation 17 using (2S)-2-[(3R)-1-tert-butoxycarbonylpyrrolidin-3-yl]-3-(3-nitrophenyl) propanoic acid and running the reaction at 80° C. in toluene as the reaction solvent. Purify the crude product by silica gel chromatography using a gradient of 5 to 20% EtOAc in hexanes. ES/MS (m/z): 309 [M+H− (2×tert-butyl)].

Preparation 19 tert-Butyl(3R)-3-[(1S)-2-tert-butoxy-1-[(3-formylphenyl)methyl]-2-oxo-ethyl]pyrrolidine-1-carboxylate

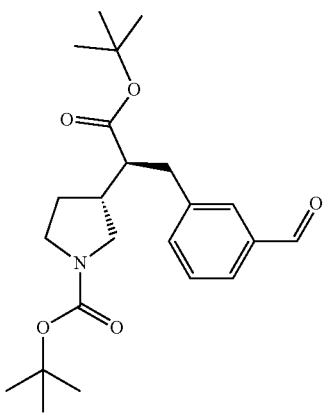 [SMILES: CC(C)(C)OC(=O)[C@@H](Cc1cccc(C=O)c1)[C@H]1CCN(C(=O)OC(C)(C)C)C1]

Add to a parr reactor a solution of tert-butyl (3R)-3-[(1S)-1-[(3-bromophenyl)methyl]-2-tert-butoxy-2-oxo-ethyl]pyrrolidine-1-carboxylate (300 g, 660 mmol) in toluene (3000 mL) followed by palladium(II) acetate (7.41 g, 33.0 mmol, 0.05 equiv), butyldi-1-adamantylphosphine (24.92 g, 66.02 mmol, 0.1 equiv) and N,N,N',N'-tetramethylethylenediamine (115 g, 149 mL, 990 mmol, 1.5 equiv). Pressurize the mixture with 70 psi of syngas (CO/H$_2$ 1:1) and stir at 100° C. overnight. Cool the mixture to RT and evaporate the solvent to dryness. Dissolve the residue in EtOAc and filter through silica gel to obtain the title compound (273 g, 97%) as an orange oil. ES/MS (m/z): 426 (M+Na).

Preparation 20 tert-Butyl(3R)-3-[2-tert-butoxy-1-[(3-formylphenyl)methyl]-1-methyl-2-oxo-ethyl]pyrrolidine-1-carboxylate

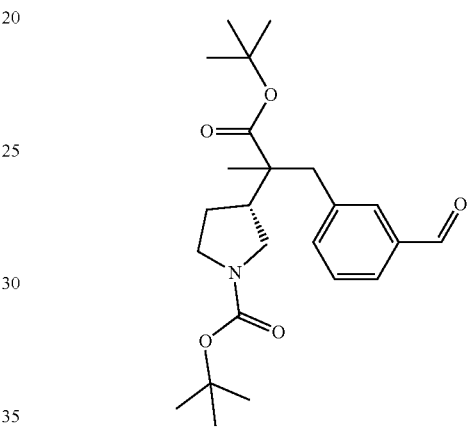

Prepare the title compound essentially as described in Preparation 19 using tert-butyl (3R)-3-[1-[(3-bromophenyl)methyl]-2-tert-butoxy-1-methyl-2-oxo-ethyl]pyrrolidine-1-carboxylate. Purify the crude product by silica gel chromatography using a gradient of 10 to 30% acetone in hexanes. ES/MS (m/z): 262 (M+H-tert-butyl-BOC).

Preparation 21 tert-Butyl (3R)-3-[(1S)-2-tert-butoxy-1-[[3-[hydroxyiminomethyl]phenyl]methyl]-2-oxo-ethyl]pyrrolidine-1-carboxylate

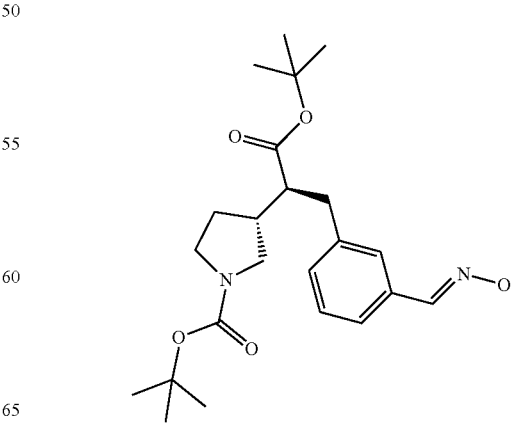

Mix tert-butyl(3R)-3-[(1S)-2-tert-butoxy-1-[(3-formylphenyl)methyl]-2-oxo-ethyl]pyrrolidine-1-carboxylate (50 g, 105 mmol, purity 85%), EtOH (400 mL), pyridine (17.0 mL, 211 mmol, 2 equiv) and hydroxylamine hydrochloride (10.98 g, 158.0 mmol, 1.5 equiv). Stir the mixture at RT for 2 h. Evaporate the solvent, add KHSO₄ (1 M solution in water, 300 mL) and MTBE (500 mL). Separate the organic layer, wash the organic layer with saturated aqueous NaHCO₃, filter and dry over MgSO₄. Filter through Celite® and concentrate to dryness to obtain the title compound as a yellow oil (49 g, 98% yield, purity 88% w/w). ES/MS (m/z): 319 (M+H-Boc)

Preparation 22 tert-Butyl (3R)-3-[(1S)-1-[[3-(aminomethyl)phenyl]methyl]-2-tert-butoxy-2-oxo-ethyl]pyrrolidine-1-carboxylate

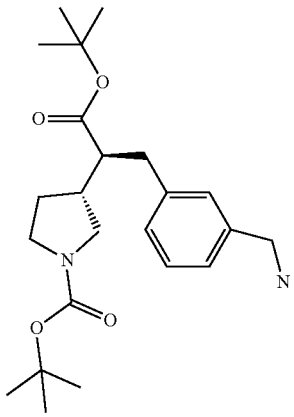 [SMILES: CC(C)(C)OC(=O)[C@@H](Cc1cccc(CN)c1)[C@H]1CCN(C(=O)OC(C)(C)C)C1]

Prepare a FlowCAT high pressure flow chemistry reactor (H.E.L Ltd) with a stainless steel packed-bed reactor column (1.2 cm inner diameter×10 cm long) containing sponge nickel catalyst (2 g) and glass beads (6 g, 212 to 300 microns). The reactor is equipped with gas and liquid flow controllers and a heating jacket around the column. Equilibrate the column by flushing with MeOH and hydrogen gas with the following parameters: liquid flow rate—4 mL/min; H₂ flow rate—60 mL/min; pressure—50 bar; reactor column jacket temperature—120° C. (internal reaction temperature maintained at 50° C.).

Dissolve tert-butyl (3R)-3-[(1S)-2-tert-butoxy-1-[[3-[hydroxyiminomethyl]phenyl]methyl]-2-oxo-ethyl]pyrrolidine-1-carboxylate (49 g, 103 mmol, purity 88% w/w) in ammonia (7 M solution in MeOH, 606 mL) and flush it through the reactor column along with hydrogen gas using the column equilibration parameters, collecting the eluate from the reactor column. Flush the column again with ammonia (7 M solution in MeOH) over 20 min, collecting the reactor column eluate. Combine the reactor column eluate fractions and concentrate the mixture in-vacuo to obtain the title compound as an oil (46.9 g, 88% yield, purity 78% w/w). ES/MS (m/z): 405 (M+H).

Preparation 23 tert-Butyl (3R)-3-[(1S)-1-[(3-aminophenyl)methyl]-2-tert-butoxy-2-oxo-ethyl]pyrrolidine-1-carboxylate

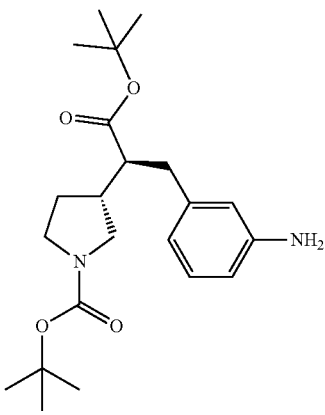 [SMILES: CC(C)(C)OC(=O)[C@@H](Cc1cccc(N)c1)[C@H]1CCN(C(=O)OC(C)(C)C)C1]

Add palladium on carbon (10% w/w, 380 mg, 0.36 mmol, 0.05 equiv) to a stirred solution of tert-butyl (3R)-3-[(1S)-2-tert-butoxy-1-[(3-nitrophenyl)methyl]-2-oxo-ethyl]pyrrolidine-1-carboxylate (3 g, 7.1 mmol) in EtOAc (71 mL) under nitrogen atmosphere. Purge the mixture with hydrogen and stir under a balloon of hydrogen at RT overnight. Filter the reaction mixture over a pad of diatomaceous earth. Concentrate the filtrate in-vacuo to give the title compound (2.62 g, 94%) as a white solid. ES/MS (m/z): 291 (M+H—BOC).

Preparation 24 tert-Butyl (3R)-3-[(1S)-2-tert-butoxy-1-[[3-(hydroxymethyl)phenyl]methyl]-2-oxo-ethyl]pyrrolidine-1-carboxylate

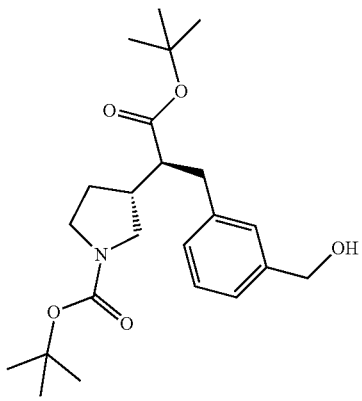 [SMILES: CC(C)(C)OC(=O)[C@@H](Cc1cccc(CO)c1)[C@H]1CCN(C(=O)OC(C)(C)C)C1]

Add sodium borohydride (0.208 g, 5.50 mmol, 1.2 equiv) to a solution of tert-butyl (3R)-3-[(1S)-2-tert-butoxy-1-[(3-formylphenyl)methyl]-2-oxo-ethyl]pyrrolidine-1-carboxylate (1.85 g, 4.58 mmol) in MeOH (25 mL) at 0° C. After 10 min, evaporate the solvent. Add saturated aqueous NaHCO₃ and extract the aqueous layer with EtOAc. Wash the organics with water and saturated aqueous NaCl. Dry the organics

Preparation 25

[3-[(2S)-3-tert-Butoxy-2-[(3R)-1-tert-butoxycarbonylpyrrolidin-3-yl]-3-oxo-propyl]phenyl]boronic acid

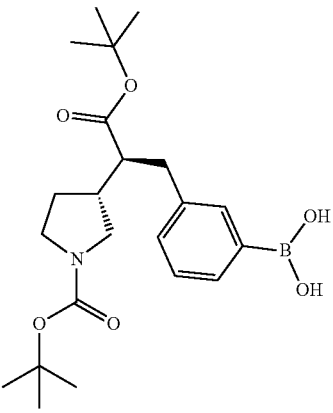 [SMILES: CC(C)(C)OC(=O)[C@@H](Cc1cccc(B(O)O)c1)[C@H]1CCN(C(=O)OC(C)(C)C)C1]

Mix tert-butyl (3R)-3-[(1S)-1-[(3-bromophenyl)methyl]-2-tert-butoxy-2-oxo-ethyl]pyrrolidine-1-carboxylate (16.4 g, 36.1 mmol), tetrahydroxydiboron (5.00 g, 54.1 mmol, 1.5 equiv), chloro(2-dicyclohexylphosphino-2',4',6'-triisopropyl-1,1'-biphenyl)[2-(2'-amino-1,1'-biphenylyl)]palladium (II) (XPhos Pd G2, 0.145 g, 0.180 mmol, 0.005 equiv), 2-dicyclohexylphosphino-2',4',6'-triisopropylbiphenyl (XPhos, 0.176 g, 0.361 mmol, 0.01 equiv), potassium acetate (10.6 g, 108 mmol, 3 equiv), EtOH (246 mL) and ethylene glycol (6.10 mL, 108 mmol, 3 equiv). Purge with nitrogen for 5 minutes. Stir the mixture at 90° C. overnight. Cool the reaction to RT, add 2-methyltetrahydrofuran (158 mL), and filter. Concentrate and use the residue in Preparation 26 without further purification. ES/MS (m/z): 308 (M+H−2×tert-butyl).

Preparation 26 tert-Butyl (3R)-3-[(1S)-2-tert-butoxy-1-[(3-hydroxyphenyl)methyl]-2-oxo-ethyl]pyrrolidine-1-carboxylate

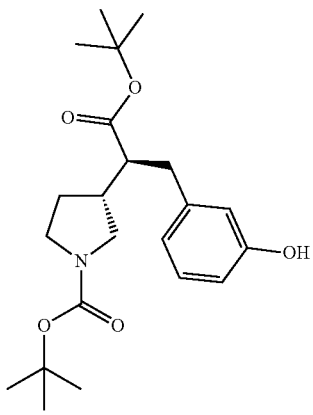 [SMILES: CC(C)(C)OC(=O)[C@@H](Cc1cccc(O)c1)[C@H]1CCN(C(=O)OC(C)(C)C)C1]

To a solution of [3-[(2S)-3-tert-butoxy-2-[(3R)-1-tert-butoxycarbonylpyrrolidin-3-yl]-3-oxo-propyl]phenyl]boronic acid (3.8 g, 8.4 mmol) in THF (42 mL) add a solution of hydrogen peroxide (30% in water, 9.1 mL, 84 mmol, 10 equiv). Stir the reaction at RT overnight. Quench the reaction slowly by the addition of a solution of sodium bisulfite (20% w/v in water, 120 mL). Extract the mixture with EtOAc twice and wash the combined organics with saturated aqueous NaCl. Dry the organics over $Na_2SO_4$, filter, and concentrate in-vacuo. Purify the residue by silica gel chromatography using a gradient of 10 to 40% acetone in hexanes to give the title compound (3.05 g, 90%) as a beige solid. ES/MS (m/z): 280 (M+H−2×tert-butyl)

Preparation 27 tert-Butyl (3R)-3-[(1S)-2-tert-butoxy-1-[[3-[[[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-oxo-ethyl]pyrrolidine-1-carboxylate

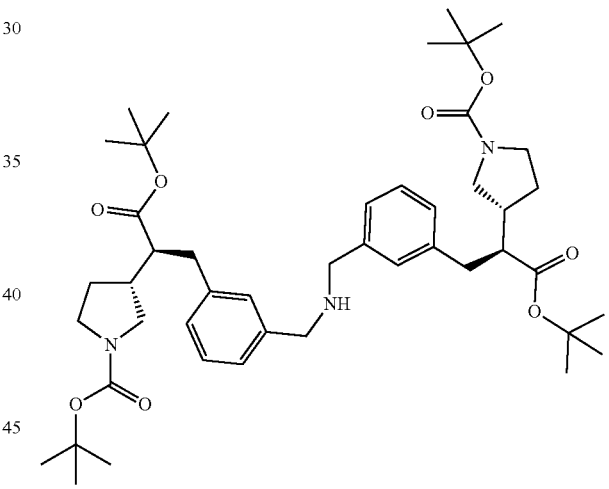

Add tert-butyl (3R)-3-[(1S)-2-tert-butoxy-1-[(3-formylphenyl)methyl]-2-oxo-ethyl]pyrrolidine-1-carboxylate (48 g, 100 mmol, purity 85% w/w, 1.1 equiv.), isopropanol (328 mL) and tert-butyl (3R)-3-[(1S)-1-[[3-(aminomethyl)phenyl]methyl]-2-tert-butoxy-2-oxo-ethyl]pyrrolidine-1-carboxylate (46.9 g, 93 mmol, purity 78%, 1 equiv) to a round bottom flask. Stir the mixture at RT for 1 h. Cool the mixture at 0° C. and add sodium triacetoxyborohydride (59 g, 280 mmol, 3 equiv) and stir the mixture at RT for 2 days. Remove the solvent under reduced pressure. Add water (200 mL), saturated aqueous $NaHCO_3$ (300 mL) and EtOAc (500 mL). Separate the organic layer and purify by silica gel chromatography using a gradient of 50 to 100% EtOAc in hexanes to obtain the title compound as a colorless oil (36 g, 42% yield, purity 85% w/w). ES/MS (m/z): 792 (M+H).

Preparation 28 tert-Butyl (3R)-3-[(1S)-1-[[3-[[bis[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-tert-butoxy-2-oxo-ethyl]pyrrolidine-1-carboxylate & tert-Butyl (3R)-3-[(1S)-2-tert-butoxy-1-[[3-[[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-oxo-ethyl]pyrrolidine-1-carboxylate

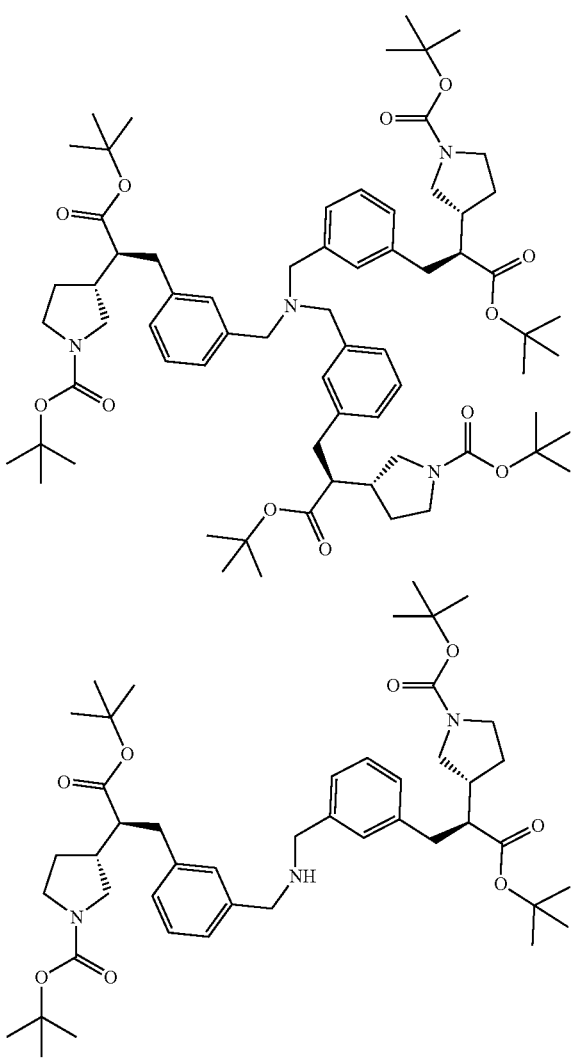

Method 1 for the Preparation of the Title Compounds as a Mixture and then Separation by Chromatography To a round bottom flask add tert-butyl (3R)-3-[(1S)-2-tert-butoxy-1-[(3-formylphenyl)methyl]-2-oxo-ethyl]pyrrolidine-1-carboxylate (222 g, 550 mmol), 2-propanol (888 mL) and a solution of ammonia (2 M in 2-propanol, 302.6 mL, 605.2 mmol, 1.1 equiv). Cool the mixture to between 0 and 5° C. with an ice-water bath. Add sodium triacetoxyborohydride (116.6 g, 550.2 mmol, 1 equiv) in four portions with 40 min between addition of each portion. Stir the mixture at RT overnight. Evaporate the solvent to dryness. To the residue add water (200 mL), aqueous $K_2HPO_4$ (300 mL) and extract the aqueous layer with MTBE (2×500 mL). Dry the organic layer over $MgSO_4$, filter and concentrate to dryness. Purify the residue by silica gel chromatography using a gradient of 20 to 80% EtOAc in hexanes to obtain tert-butyl (3R)-3-[(1S)-1-[[3-[[bis[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-tert-butoxy-2-oxo-ethyl]pyrrolidine-1-carboxylate (57.8 g, 27%) as a white solid. $^1$H-NMR (400 MHz, $CDCl_3$) δ 7.30-7.24 (m, 6H), 7.12 (s, 3H), 7.04 (s, 3H), 3.75-3.43 (m, 12H), 3.30-3.21 (m, 3H), 3.10-2.96 (m, 3H), 2.89-2.76 (m, 6H), 2.49 (d, J=4.7 Hz, 3H), 2.37 (dd, J=7.2, 14.4 Hz, 3H), 1.98-1.90 (m, 3H), 1.74-1.61 (m, 3H), 1.48 (s, 27H), 1.22 (s, 27H).

From the silica gel chromatography above, also obtain tert-butyl (3R)-3-[(1S)-2-tert-butoxy-1-[[3-[[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-oxo-ethyl]pyrrolidine-1-carboxylate (82.50 g, 34%) as a colorless oil. ES/MS (m/z): 792 (M+H), HPLC shows 90 wt % purity.

Method 2 for the preparation of tert-butyl (3R)-3-[(1S)-1-[[3-[[bis[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-tert-butoxy-2-oxo-ethyl]pyrrolidine-1-carboxylate To a round bottom flask add tert-butyl (3R)-3-[(1S)-2-tert-butoxy-1-[[3-[[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-oxo-ethyl]pyrrolidine-1-carboxylate (90 wt % pure, 81.5 g, 92.6 mmol), tert-butyl (3R)-3-[(1S)-2-tert-butoxy-1-[(3-formylphenyl)methyl]-2-oxo-ethyl]pyrrolidine-1-carboxylate (85 wt % pure, 50.6 g, 106 mmol, 1.15 equiv), 2-propanol (652 mL) and acetic acid (5.31 mL, 92.6 mmol, 1 equiv) and stir the mixture for 30 min. Add sodium triacetoxyborohydride (2 equiv, 185 mmol, 39.3 g) to the mixture and stir at RT for 2 h, then concentrate the reaction mixture in-vacuo. Add water (200 mL) and MTBE (300 mL) to the residue and then add concentrated aqueous ammonium hydroxide to adjust to pH 9-10. Separate the organic phase and dry over $MgSO_4$, filter, and concentrate to dryness. Purify the residue by silica gel chromatography using a gradient of 20 to 40% EtOAc in hexanes to obtain tert-butyl (3R)-3-[(1S)-1-[[3-[[bis[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-tert-butoxy-2-oxo-ethyl]pyrrolidine-1-carboxylate (89 g, 82%) as a white solid.

Preparation 29 tert-Butyl (3R)-3-[(1S)-2-tert-butoxy-1-[[3-[[[3-[(2S)-3-tert-butoxy-2-[(3R)-1-tert-butoxycarbonylpyrrolidin-3-yl]-3-oxo-propyl]phenyl]methyl-[(3-fluoro-5-methoxy-phenyl)methyl]amino]methyl]phenyl]methyl]-2-oxo-ethyl]pyrrolidine-1-carboxylate

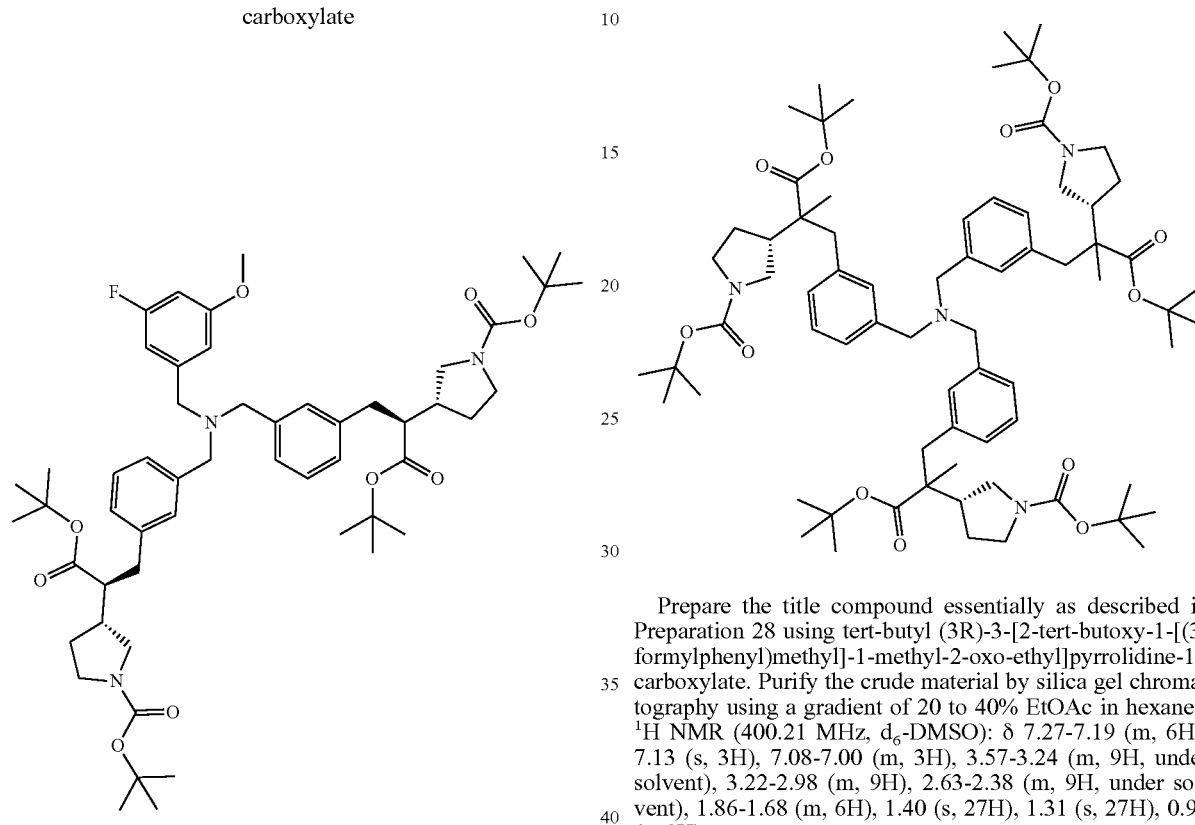

Mix tert-butyl (3R)-3-[(1 S)-2-tert-butoxy-1-[[3-[[[3-(2S)-3-tert-butoxy-2-[(3R)-1-tert-butoxycarbonylpyrrolidin-3-yl]-3-oxo-propyl]phenyl]methyl]amino]methyl]phenyl]methyl]-2-oxo-ethyl]pyrrolidine-1-carboxylate (36 g, 39 mmol, purity 85%), 3-fluoro-5-methoxybenzaldehyde (6.684 g, 42.49 mmol, 1.1 equiv), isopropanol (288 mL) and sodium triacetoxyborohydride (16.38 g, 77.26 mmol, 2 equiv) and stir the mixture at RT for 2 h. Evaporate the solvent. Add saturated aqueous NaHCO₃ (500 mL) and extract the aqueous layer with EtOAc (500 mL). Dry the organic layer over MgSO₄, then filter and concentrate to dryness. Purify by silica gel chromatography using a gradient of 10 to 40% EtOAc in hexanes to obtain the title compound as a colorless oil (32 g, 76% yield, purity 85% w/w). ES/MS (m/z): 931 (M+H).

Preparation 30 tert-butyl (3R)-3-[1-[[3-[[bis[[3-[3-tert-butoxy-2-[(3R)-1-tert-butoxycarbonylpyrrolidin-3-yl]-2-methyl-3-oxo-propyl]phenyl]methyl]amino]methyl]phenyl]methyl]-2-tert-butoxy-1-methyl-2-oxo-ethyl]pyrrolidine-1-carboxylate

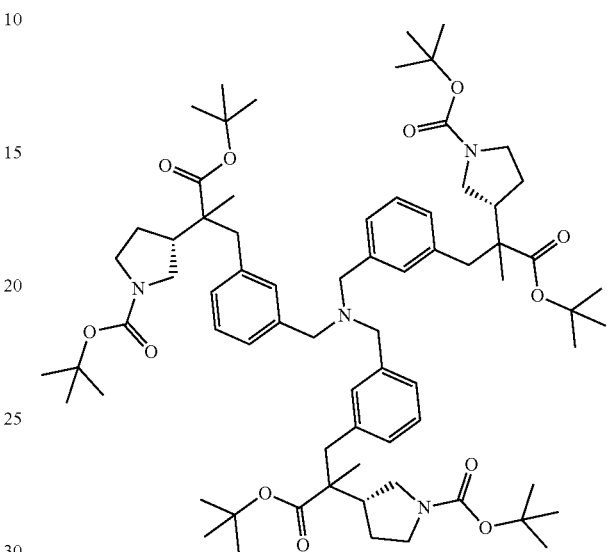

Prepare the title compound essentially as described in Preparation 28 using tert-butyl (3R)-3-[2-tert-butoxy-1-[(3-formylphenyl)methyl]-1-methyl-2-oxo-ethyl]pyrrolidine-1-carboxylate. Purify the crude material by silica gel chromatography using a gradient of 20 to 40% EtOAc in hexanes. ¹H NMR (400.21 MHz, d₆-DMSO): δ 7.27-7.19 (m, 6H), 7.13 (s, 3H), 7.08-7.00 (m, 3H), 3.57-3.24 (m, 9H, under solvent), 3.22-2.98 (m, 9H), 2.63-2.38 (m, 9H, under solvent), 1.86-1.68 (m, 6H), 1.40 (s, 27H), 1.31 (s, 27H), 0.93 (s, 9H).

Preparation 31 tert-Butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenoxy]phenyl]methyl]-2-oxo-ethyl]pyrrolidine-1-carboxylate

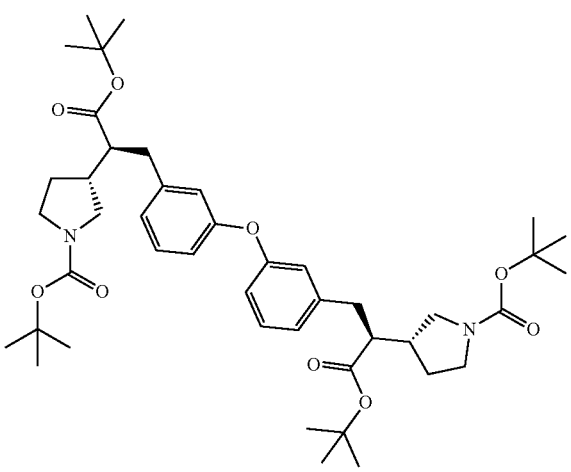 [SMILES: CC(C)(C)OC(=O)[C@@H](Cc1cccc(Oc2cccc(C[C@H](C(=O)OC(C)(C)C)[C@H]3CCN(C(=O)OC(C)(C)C)C3)c2)c1)[C@H]1CCN(C(=O)OC(C)(C)C)C1]

Mix tert-butyl (3R)-3-[(1S)-1-[(3-bromophenyl)methyl]-2-tert-butoxy-2-oxo-ethyl]pyrrolidine-1-carboxylate (150 mg, 0.330 mmol), tert-butyl (3R)-3-[(1S)-2-tert-butoxy-1-[(3-hydroxyphenyl)methyl]-2-oxo-ethyl]pyrrolidine-1-carboxylate (0.155 g, 0.396 mmol, 1.2 equiv), cuprous iodide (6 mg, 0.03 mmol, 0.1 equiv), N,N-dimethylglycine hydrochloride (0.0138 g, 0.0990 mmol, 0.3 equiv) and cesium carbonate (0.215 g, 0.660 mmol, 2 equiv) in DMF (2.3 mL). Stir the mixture under nitrogen at 110° C. overnight. Cool the reaction, then filter through a pad of diatomaceous earth, washing with DCM and MeOH. Concentrate the filtrate in-vacuo. Purify the resulting residue by RP-HPLC/MS using the following parameters: column—XBridge™ C18 (19×100 mm, µm); mobile phase—solvent A=20 mM ammonium bicarbonate in water (pH 9), solvent B=acetonitrile; gradient—0:100 to 100:0 B:A; flow rate—25 mL/min. Obtain the title compound (43 mg, 17%). ES/MS (m/z): 665 (M+H—BOC).

Preparation 32 tert-Butyl (3R)-3-[(1S)-2-tert-butoxy-1-[[3-[2-[3-[(2S)-3-tert-butoxy-2-[(3R)-1-tert-butoxycarbonylpyrrolidin-3-yl]-3-oxo-propyl]phenoxy]ethoxy]phenyl]methyl]-2-oxo-ethyl]pyrrolidine-1-carboxylate

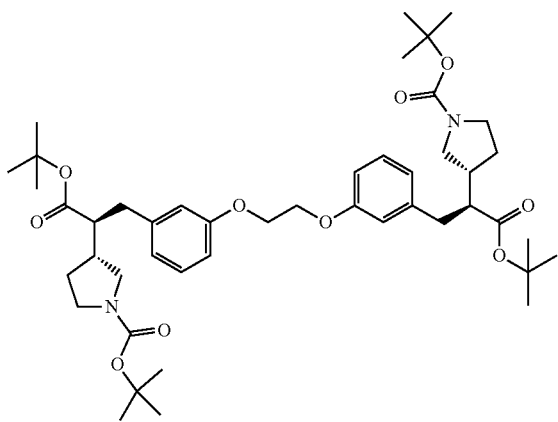 [SMILES: CC(C)(C)OC(=O)[C@@H](Cc1cccc(OCCOc2cccc(C[C@H](C(=O)OC(C)(C)C)[C@H]3CCN(C(=O)OC(C)(C)C)C3)c2)c1)[C@H]1CCN(C(=O)OC(C)(C)C)C1]

Dissolve tert-butyl (3R)-3-[(1S)-2-tert-butoxy-1-[(3-hydroxyphenyl)methyl]-2-oxo-ethyl]pyrrolidine-1-carboxylate (275 mg, 0.70 mmol) in DMF (1.2 mL). Add cesium carbonate (285 mg, 0.86 mmol) and 1,2-dibromoethane (0.030 mL, 0.34 mmol) and stir at RT for 3 days. Along the following 9 days, add three additional portions of cesium carbonate or potassium carbonate and 1,2-dibromoethane and increase stepwise the temperature to 70 and 110° C. Cool the mixture at RT and add saturated aqueous NH₄Cl. Extract the aqueous layer with EtOAc. Wash the organic phase with saturated aqueous NaCl and water. Dry the organic phase over MgSO₄, filter and concentrate the solution in-vacuo. Purify the residue by silica gel chromatography using a gradient of 0 to 30% EtOAc in hexanes to give the title compound (33.4 mg, 11%) as a colorless oil. ES/MS (m/z): 709 (M+H—BOC).

Preparation 33 tert-Butyl (3R)-3-[(1S)-2-tert-butoxy-1-[[3-[[3-[(2S)-3-tert-butoxy-2-[(3R)-1-tert-butoxycarbonylpyrrolidin-3-yl]-3-oxo-propyl]phenoxy]methyl]phenyl]methyl]-2-oxo-ethyl]pyrrolidine-1-carboxylate

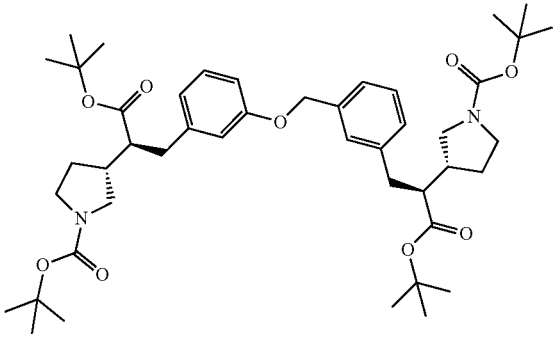 [SMILES: CC(C)(C)OC(=O)[C@@H](Cc1cccc(COc2cccc(C[C@H](C(=O)OC(C)(C)C)[C@H]3CCN(C(=O)OC(C)(C)C)C3)c2)c1)[C@H]1CCN(C(=O)OC(C)(C)C)C1]

Add triphenylphosphine (0.5733 g, 2.164 mmol, 1.5 equiv) to a solution of tert-butyl (3R)-3-[(1S)-2-tert-butoxy-1-[[3-(hydroxymethyl)phenyl]methyl]-2-oxo-ethyl]pyrrolidine-1-carboxylate (585 mg, 1.443 mmol) and tert-butyl (3R)-3-[(1S)-2-tert-butoxy-1-[(3-hydroxyphenyl)methyl]-2-oxo-ethyl]pyrrolidine-1-carboxylate (0.8472 g, 2.164 mmol, 1.5 equiv) in THF (14 mL). Purge with nitrogen and then add drop-wise diethyl azodicarboxylate (0.34 mL, 2.2 mmol, 1.5 equiv). Stir the mixture overnight at RT. Filter the reaction through a pad of diatomaceous earth, then wash with DCM and MeOH. Concentrate the filtrate in-vacuo. Purify the resulting residue by SFC with the following parameters: column—Chiracel® OD (5 µm, 2×25 cm); mobile phase—solvent A=CO2, solvent B=MeOH+DMEA (1.0% v/v); gradient—isocratic 80:20 A:B; flow rate—80 mL/min; pressure—120 bar; column temperature—40° C. Obtain the title compound (315 mg, 28%). ES/MS (m/z): 679 (M+H—BOC).

Preparation 34 tert-Butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenyl]sulfanylphenyl]methyl]-2-oxo-ethyl]pyrrolidine-1-carboxylate

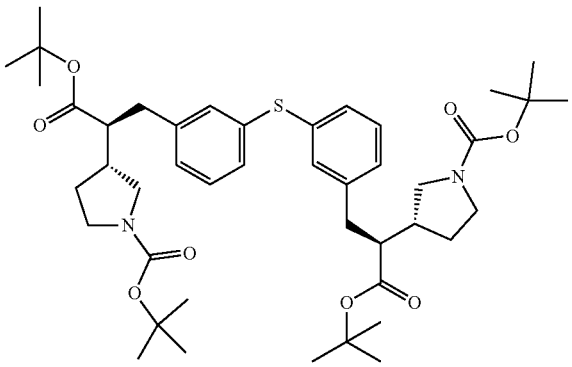 [SMILES: CC(C)(C)OC(=O)[C@@H](Cc1cccc(Sc2cccc(C[C@H](C(=O)OC(C)(C)C)[C@H]3CCN(C(=O)OC(C)(C)C)C3)c2)c1)[C@H]1CCN(C(=O)OC(C)(C)C)C1]

Add dry toluene (0.9 mL) and acetone (1.8 mL) to a mixture of tert-butyl (3R)-3-[(1S)-1-[(3-bromophenyl)methyl]-2-tert-butoxy-2-oxo-ethyl]pyrrolidine-1-carboxylate (796 mg, 1.75 mmol), potassium phosphate tribasic (229 mg, 1.06 mmol), bis(dibenzylideneacetone)palladium (50 mg, 0.09 mmol), 1,1'-bis(diphenylphosphino)ferrocene (70 mg, 0.12 mmol) and potassium thioacetate (103 mg, 0.90 mmol). Sonicate the resulting mixture for five minutes under a nitrogen atmosphere, then stir at 110° C. for 6 h. Add saturated aqueous NH₄Cl and EtOAc. Wash the organic layer with water. Dry the organic phase over MgSO₄, filter, and concentrate in-vacuo. Purify the residue by silica gel chromatography using a gradient of 0 to 40% EtOAc in hexanes to give the title compound as a yellow oil (370 mg, 52%). ES/MS (m/z): 781 (M+H).

Preparation 35 tert-Butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenyl]sulfinylphenyl]methyl]-2-oxo-ethyl]pyrrolidine-1-carboxylate

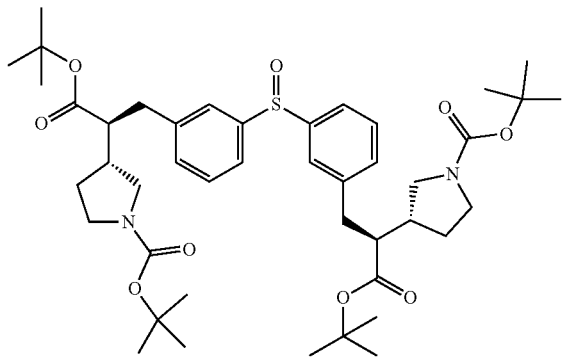 [SMILES: CC(C)(C)OC(=O)[C@@H](Cc1cccc(S(=O)c2cccc(C[C@H](C(=O)OC(C)(C)C)[C@H]3CCN(C(=O)OC(C)(C)C)C3)c2)c1)[C@H]1CCN(C(=O)OC(C)(C)C)C1]

Dissolve tert-butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenyl]sulfanylphenyl]methyl]-2-oxo-ethyl]pyrrolidine-1-carboxylate (111 mg, 0.14 mmol) in DCM (2 mL). Add 3-chloroperoxybenzoic acid (34 mg, 0.14 mmol, 1 equiv). Stir the mixture at RT for 3 h. Add saturated aqueous NaHCO₃ followed by DCM and separate the layers. Wash the organic phase with a solution of NaOH (3% w/v in water) and with water. Dry the organic phase over MgSO₄, then filter and concentrate the solution in-vacuo. Purify the residue by silica gel chromatography using a gradient of 0 to 60% EtOAc in hexanes to give the title compound (97.2 mg, 87%) as a colorless oil. ES/MS (m/z): 697 (M+H—BOC).

Preparation 36 tert-Butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenyl]sulfonylphenyl]methyl]-2-oxo-ethyl]pyrrolidine-1-carboxylate

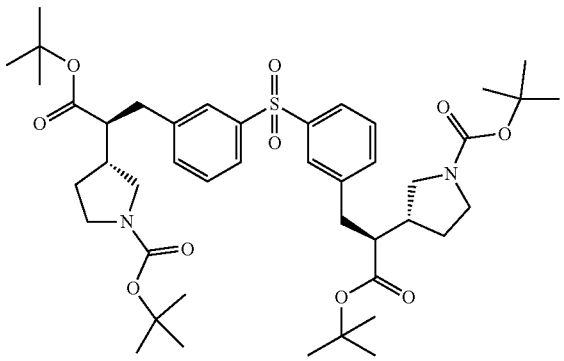 [SMILES: CC(C)(C)OC(=O)[C@@H](Cc1cccc(S(=O)(=O)c2cccc(C[C@H](C(=O)OC(C)(C)C)[C@H]3CCN(C(=O)OC(C)(C)C)C3)c2)c1)[C@H]1CCN(C(=O)OC(C)(C)C)C1]

The compound is prepared in a manner essentially analogous to the method of the Preparation 35 but using 2.5 equiv of 3-chloroperoxybenzoic acid. Purify the crude product by silica gel chromatography using a gradient of 20 to 60% EtOAc in hexanes to give the title compound (116.6 mg, 82%) as a white solid. ES/MS (m/z): 713 (M+H—BOC).

Preparation 37 tert-Butyl (3R)-3-[(1S)-2-tert-butoxy-1-[[3-[[3-[(2S)-3-tert-butoxy-2-[(3R)-1-tert-butoxycarbonylpyrrolidin-3-yl]-3-oxo-propyl]anilino]methyl]phenyl]methyl]-2-oxo-ethyl]pyrrolidine-1-carboxylate

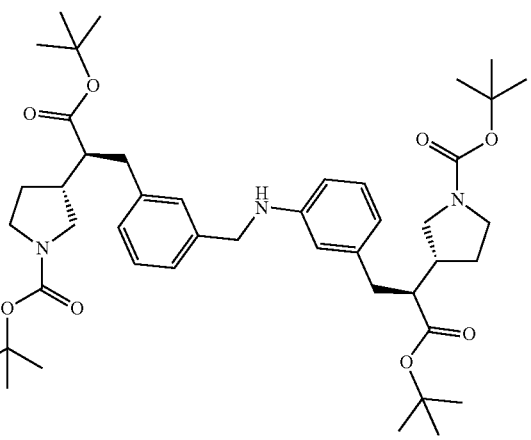

Add sodium triacetoxyborohydride (543 mg, 2.56 mmol, 2 equiv) to a solution of tert-butyl (3R)-3-[(1S)-1-[(3-aminophenyl)methyl]-2-tert-butoxy-2-oxo-ethyl]pyrrolidine-1-carboxylate (500 mg, 1.28 mmol), tert-butyl (3R)-3-[(1S)-2-tert-butoxy-1-[(3-formylphenyl)methyl]-2-oxo-ethyl]pyrrolidine-1-carboxylate (620 mg, 1.54 mmol, 1.2 equiv) and acetic acid (220 uL, 3.84 mmol, 3 equiv). Stir at RT for 4 days. Add saturated aqueous NaHCO₃ and extract the aqueous layer with DCM. Dry the combined organic layers over MgSO₄, filter and concentrate the solution in-vacuo. Purify the residue by silica gel chromatography using a gradient of 10 to 50% EtOAc in hexanes to give the title compound (850 mg, 72%). ES/MS (m/z): 778 (M+H).

Preparation 38

(2S)-3-[3-[3-[(2S)-3-tert-Butoxy-2-[(3R)-1-tert-butoxycarbonylpyrrolidin-3-yl]-3-oxo-propyl]anilino]phenyl]-2-[(3R)-1-tert-butoxycarbonylpyrrolidin-3-yl]propanoic acid

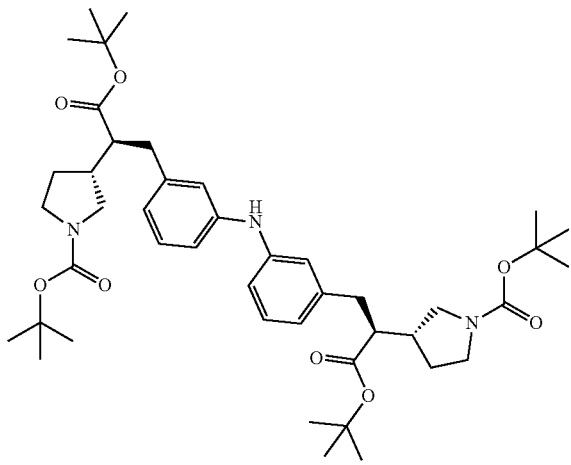 [SMILES: CC(C)(C)OC(=O)[C@@H](Cc1cccc(Nc2cccc(C[C@H](C(=O)OC(C)(C)C)[C@H]3CCN(C(=O)OC(C)(C)C)C3)c2)c1)[C@H]1CCN(C(=O)OC(C)(C)C)C1]

Mix (2S)-3-(3-bromophenyl)-2-[(3R)-1-tert-butoxycarbonylpyrrolidin-3-yl]propanoic acid (8 g, 20 mmol) in 1,4-dioxane (160 mL), tert-butyl (3R)-3-[(1S)-1-[(3-aminophenyl)methyl]-2-tert-butoxy-2-oxo-ethyl]pyrrolidine-1-carboxylate (8.628 g, 22.09 mmol, 1.1 equiv) and potassium carbonate (4 equiv., 11.22 g, 80.34 mmol). Heat the mixture at 60° C. for 15 min under nitrogen. Add [(2-di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3, 0.371 g, 0.402 mmol, 0.02 equiv) and heat the reaction at 100° C. with stirring overnight. Cool the reaction to RT, dilute with EtOAc, and adjust the pH of the mixture to less than 3 by the addition of aqueous HCl (1 N). Extract the aqueous layer with Me-THF three times. Wash the combined organics with saturated aqueous NaCl. Dry the organics over MgSO₄ and concentrate the solution in-vacuo. Purify the residue by silica gel chromatography using a gradient of 0 to 100% EtOAc in hexanes to give the title compound (9.5 g, 67%). ES/MS (m/z): 608 (M+H—BOC)

Preparation 39

Di-tert-butyl 3,3'-((2S,2'S)-((sulfonylbis(azanediyl))bis(3,1-phenylene))bis(3-(tert-butoxy)-3-oxopropane-1,2-diyl))(3R,3'R)-bis(pyrrolidine-1-carboxylate)

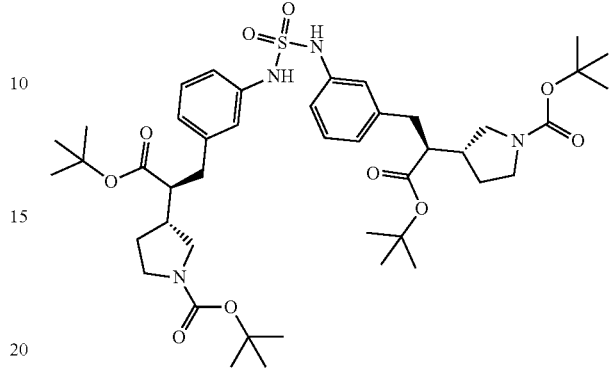

Cool to 0° C. a solution of 1,4-diazabicyclo[2.2.2]octane bis(sulfur dioxide) adduct (DABSO, 0.6279 g, 2.561 mmol, 2 equiv) in acetonitrile (12.8 mL). Add iodine (0.4875 g, 1.921 mmol, 1.5 equiv). Stir the mixture at 0° C. for 15 min and then add tert-butyl (3R)-3-[(1S)-1-[(3-aminophenyl)methyl]-2-tert-butoxy-2-oxo-ethyl]pyrrolidine-1-carboxylate (500 mg, 1.280 mmol). Heat the reaction to 80° C. overnight. Cool the reaction, filter through a pad of diatomaceous earth and wash the pad with DCM and MeOH. Concentrate the filtrate in-vacuo. Purify the residue by RP-HPLC/MS with the following parameters: column—XBridge™ C18 (19×100 mm, 5 μm); mobile phase—solvent A=20 mM aqueous ammonium bicarbonate (pH 9), solvent B=acetonitrile; gradient—isocratic 80:20 A:B; flow rate—25 mL/min; RT. Obtain the title compound (195 mg, 18%) as a pale yellow solid. ES/MS (m/z): 743 (M+H—BOC).

EXAMPLE 1

(2S)-3-[3-[[Bis[[3-[(2S)-2-carboxy-2-[(3R)-pyrrolidin-3-yl]ethyl]phenyl]methyl]amino]methyl]phenyl]-2-[(3R)-pyrrolidin-3-yl]propanoic acid; tetrahydrochloride

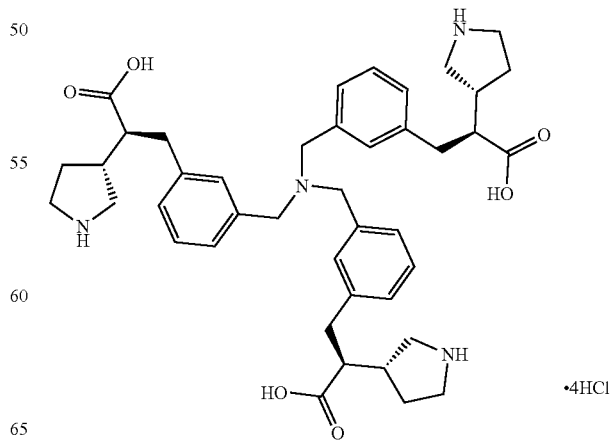

Add a solution of hydrochloric acid (4M in 1,4-dioxane, 67 mL, 270 mmol, 20 equiv) to tert-butyl (3R)-3-[(1S)-1-[[3-[[bis[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-tert-butoxy-2-oxo-ethyl]pyrrolidine-1-carboxylate (15.7 g, 13.3 mmol) and stir the mixture at 40° C. overnight. Cool the mixture to RT and then concentrate to dryness. Dissolve the residue in water (40 mL) and lyophilize. Dissolve the resulting solid in water (40 mL) again and lyophilize to obtain the title compound (8.6 g, 75%) as a white foam. ES/MS (m/z): 711 (M+H); $^1$H-NMR (500 MHz, D$_2$O) δ 7.35-7.10 (m, 12H), 4.25-4.17 (m, 6H), 3.55 (dd, J=8.1, 11.5 Hz, 3H), 3.38-3.33 (m, 3H), 3.22-3.15 (m, 3H), 3.03-2.87 (m, 12H), 2.56-2.45 (m, 3H), 2.12-2.08 (m, 3H), 1.73-1.63 (m, 3H).

EXAMPLE 2

(2S)-3-[3-[[bis[[3-[(2S)-2-carboxy-2-[(3R)-pyrrolidin-3-yl]ethyl]phenyl]methyl]amino]methyl]phenyl]-2-[(3R)-pyrrolidin-3-yl]propanoic acid

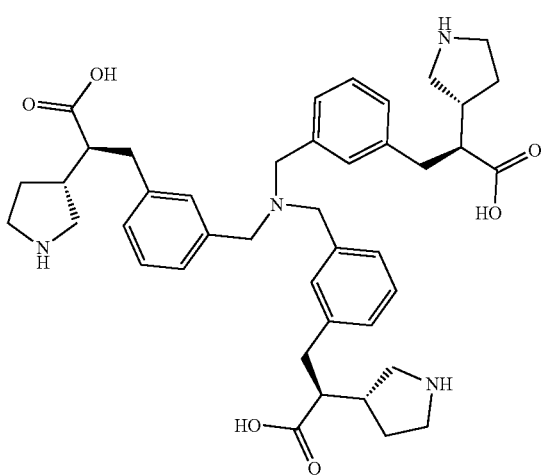 [SMILES: O=C(O)[C@@H](Cc1cccc(CN(Cc2cccc(C[C@H](C(=O)O)[C@H]3CCNC3)c2)Cc2cccc(C[C@H](C(=O)O)[C@H]3CCNC3)c2)c1)[C@H]1CCNC1]

To a round bottom flask add tert-butyl (3R)-3-[(1S)-1-[[3-[[bis[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-tert-butoxy-2-oxo-ethyl]pyrrolidine-1-carboxylate (499.3 g, 423.3 mmol), 1,4-dioxane (1997 mL), and a solution of hydrochloric acid (12 M in water, 529.1 mL, 15 equiv). Stir the mixture at 40° C. for 1 h and then concentrate the mixture in-vacuo to remove 1,4-dioxane, resulting in an aqueous slurry. Filter the mixture through a propylene filter to eliminate insoluble particles. Adjust the pH of the filtrate to 9-10 using a solution of NaOH (2M in water). Stir the mixture at RT overnight. Filter off the resulting solid slowly using paper filter (slow filtration, use low vacuum). Wash the solid with water and dry under vacuum at 45° C. to obtain the title compound (281 g, 88%) as a white crystalline solid. ES/MS (m/z): 711 (M+H); $^1$H-NMR (500 MHz, D$_2$O) δ 7.33 (t, J=7.6 Hz, 3H), 7.27 (d, J=7.8 Hz, 3H), 7.13 (d, J=7.8 Hz, 3H), 7.09 (s, 3H), 4.20 (s, 6H), 3.54 (dd, J=7.9, 11.6 Hz, 3H), 3.39-3.34 (m, 3H), 3.23-3.17 (m, 3H), 3.02-2.98 (m, 3H), 2.84 (dd, J=4.6, 13.7 Hz, 3H), 2.76 (dd, J=10.6, 13.3 Hz, 3H), 2.60 (td, J=9.9, 4.8 Hz, 3H), 2.48 (td, J=17.3, 9.6 Hz, 3H), 2.12-2.07 (m, 3H), 1.73-1.65 (m, 3H).

EXAMPLE 3

(2S)-3-[3-[[[3-[(2S)-2-Carboxy-2-[(3R)-pyrrolidin-3-yl]ethyl]phenyl]methylamino]methyl]phenyl]-2-[(3R)-pyrrolidin-3-yl]propanoic acid; trihydrochloride

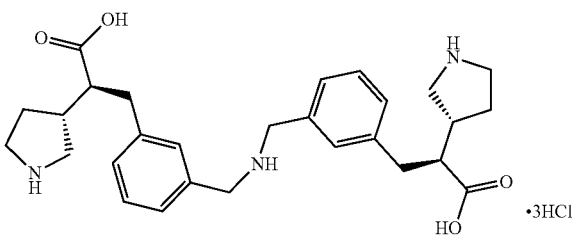 [SMILES: O=C(O)[C@@H](Cc1cccc(CNCc2cccc(C[C@H](C(=O)O)[C@H]3CCNC3)c2)c1)[C@H]1CCNC1]

Prepare the title compound essentially as described for Example 1, using tert-butyl (3R)-3-[(1S)-2-tert-butoxy-1-[[3-[[[3-[(2S)-3-tert-butoxy-2-[(3R)-1-tert-butoxycarbonylpyrrolidin-3-yl]-3-oxo-propyl]phenyl]methyl]amino]methyl]phenyl]methyl]-2-oxo-ethyl]pyrrolidine-1-carboxylate and 2 M HCl in Et$_2$O at RT. ES/MS (m/z): 480 (M+H).

EXAMPLE 4

(2S)-3-[3-[[[3-[(2S)-2-Carboxy-2-[(3R)-pyrrolidin-3-yl]ethyl]phenyl]methyl-[(3-fluoro-5-methoxyphenyl)methyl]amino]methyl]phenyl]-2-[(3R)-pyrrolidin-3-yl]propanoic acid

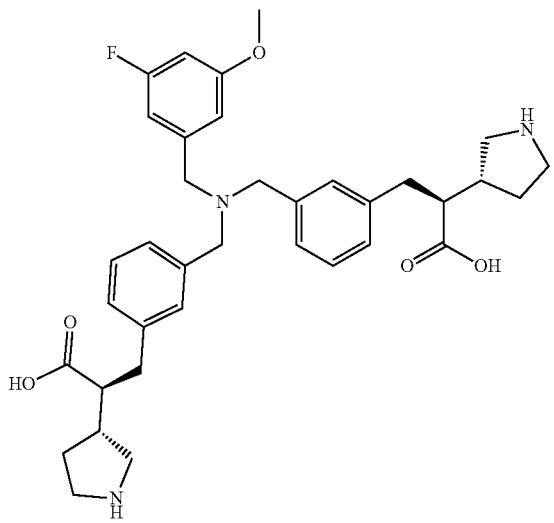 [SMILES: COc1cc(F)cc(CN(Cc2cccc(C[C@H](C(=O)O)[C@H]3CCNC3)c2)Cc2cccc(C[C@H](C(=O)O)[C@H]3CCNC3)c2)c1]

Prepare the title compound essentially as described for Example 2 using tert-butyl (3R)-3-[(1S)-2-tert-butoxy-1-[[3-[[[3-[(2S)-3-tert-butoxy-2-[(3R)-1-tert-butoxycarbonylpyrrolidin-3-yl]-3-oxo-propyl]phenyl]methyl-[(3-fluoro-5-methoxy-phenyl)methyl]amino]methyl]phenyl]methyl]-2-oxo-ethyl]pyrrolidine-1-carboxylate. ES/MS (m/z): 618 (M+H).

EXAMPLE 5

(2S)-3-[3-[[[3-[(2S)-2-Carboxy-2-[(3R)-pyrrolidin-3-yl]ethyl]phenyl]methyl-[(3-fluoro-5-methoxy-phenyl)methyl]amino]methyl]phenyl]-2-[(3R)-pyrrolidin-3-yl]propanoic acid; trihydrochloride

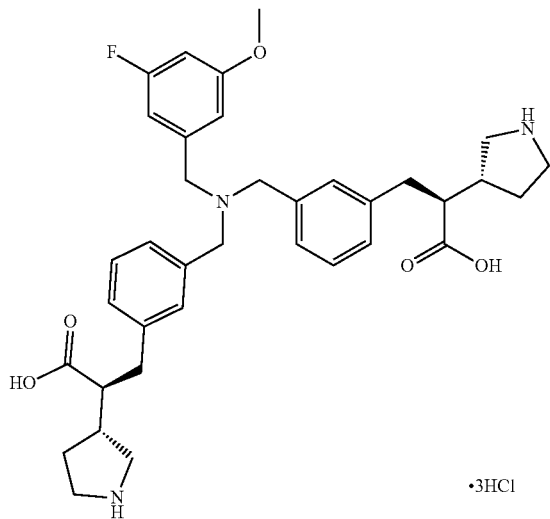 [SMILES: COc1cc(F)cc(CN(Cc2cccc(C[C@H](C(=O)O)[C@H]3CCNC3)c2)Cc2cccc(C[C@H](C(=O)O)[C@H]3CCNC3)c2)c1]

•3HCl

Mix tert-butyl (3R)-3-[(1S)-2-tert-butoxy-1-[[3-[[[3-[(2S)-3-tert-butoxy-2-[(3R)-1-tert-butoxycarbonylpyrrolidin-3-yl]-3-oxo-propyl]phenyl]methyl-[(3-fluoro-5-methoxy-phenyl)methyl]amino]methyl]phenyl]methyl]-2-oxo-ethyl]pyrrolidine-1-carboxylate (541 mg, 0.582 mmol), HCl (2 M solution in diethyl ether, 5.8 mL) and water (0.5 mL). Stir the mixture at RT for 5 h. Eliminate the solvent under reduced pressure to obtain the title compound (434 mg, 102%). ES/MS (m/z): 618 (M+H).

EXAMPLE 6

3-[3-[[bis[[3-[2-carboxy-2-[(3R)-pyrrolidin-3-yl]propyl]phenyl]methyl]amino]methyl]phenyl]-2-methyl-2-[(3R)-pyrrolidin-3-yl]propanoic acid; tetrahydrochloride

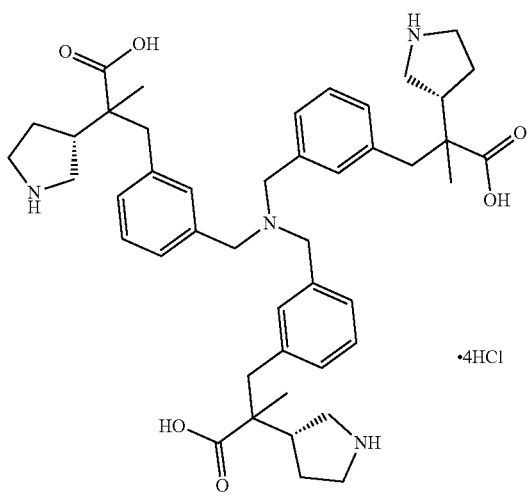 [SMILES: CC(Cc1cccc(CN(Cc2cccc(CC(C)(C(=O)O)[C@H]3CCNC3)c2)Cc2cccc(CC(C)(C(=O)O)[C@H]3CCNC3)c2)c1)(C(=O)O)[C@H]1CCNC1]

•4HCl

Mix tert-butyl (3R)-3-[1-[[3-[[bis[[3-[3-tert-butoxy-2-[(3R)-1-tert-butoxycarbonylpyrrolidin-3-yl]-2-methyl-3-oxo-propyl]phenyl]methyl]amino]methyl]phenyl]methyl]-2-tert-butoxy-1-methyl-2-oxo-ethyl]pyrrolidine-1-carboxylate (275 mg, 0.225 mmol) in DCM (1.4 mL) and add HCl (2 M solution in Et₂O, 3.4 mL, 6.7 mmol, 30 equiv). Stir the mixture at RT overnight. Decant the reaction solvent from the white solid and dissolve the solid in water. Evaporate the mixture to dryness under a stream of nitrogen, then dry in-vacuo at 40° C. to give the title compound (190 mg, 86%) as a white solid. ES/MS (m/z): 753 (M+H).

EXAMPLE 7

(2S)-3-[3-[3-[(2S)-2-carboxy-2-[(3R)-pyrrolidin-3-yl]ethyl]phenoxy]phenyl]-2-[(3R)-pyrrolidin-3-yl]propanoicacid; dihydrochloride

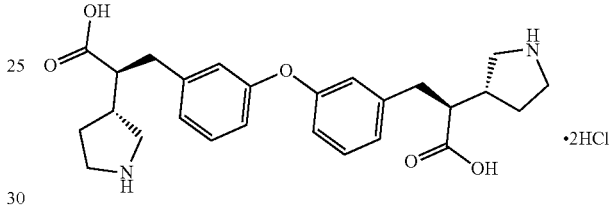

•2HCl

Prepare the title compound essentially as described in Example 6 using tert-butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenoxy]phenyl]methyl]-2-oxo-ethyl]pyrrolidine-1-carboxylate. ES/MS (m/z): 453 (M+H).

EXAMPLE 8

(2S)-3-[3-[2-[3-[(2S)-2-carboxy-2-[(3R)-pyrrolidin-3-yl]ethyl]phenoxy]ethoxy]phenyl]-2-[(3R)-pyrrolidin-3-yl]propanoic acid; dihydrochloride

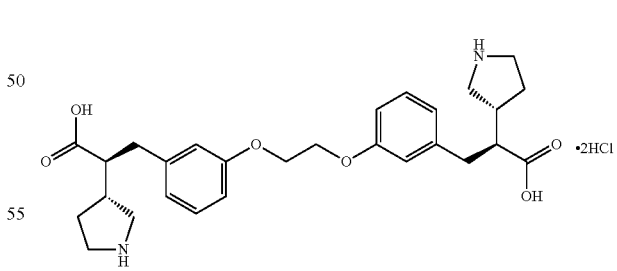

•2HCl

Prepare the title compound essentially as described in Example 6 using tert-butyl (3R)-3-[(1S)-2-tert-butoxy-1-[[3-[2-[3-[(2S)-3-tert-butoxy-2-[(3R)-1-tert-butoxycarbonylpyrrolidin-3-yl]-3-oxo-propyl]phenoxy]ethoxy]phenyl]methyl]-2-oxo-ethyl]pyrrolidine-1-carboxylate. Isolate the product by trituration with MTBE. ES/MS (m/z): 497 (M+H).

EXAMPLE 9

(2S)-3-[3-[[3-[(2S)-2-Carboxy-2-[(3R)-pyrrolidin-3-yl]ethyl]phenoxy]methyl]phenyl]-2-[(3R)-pyrrolidin-3-yl]propanoic acid; dihydrochloride

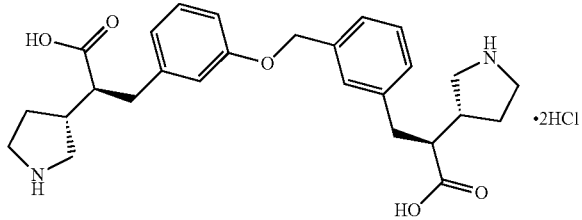 [SMILES: O=C(O)[C@@H](Cc1cccc(COc2cccc(C[C@H](C(=O)O)[C@H]3CCNC3)c2)c1)[C@H]1CCNC1]

Prepare the title compound essentially as described in Example 6 using tert-butyl (3R)-3-[(1S)-2-tert-butoxy-1-[[3-[[3-[(2S)-3-tert-butoxy-2-[(3R)-1-tert-butoxycarbonylpyrrolidin-3-yl]-3-oxo-propyl]phenoxy]methyl]phenyl]methyl]-2-oxo-ethyl]pyrrolidine-1-carboxylate. ES/MS (m/z): 467 (M+H).

EXAMPLE 10

(2S)-3-[3-[3-[(2S)-2-Carboxy-2-[(3R)-pyrrolidin-3-yl]ethyl]phenyl]sulfanylphenyl]-2-[(3R)-pyrrolidin-3-yl]propanoic acid; dihydrochloride

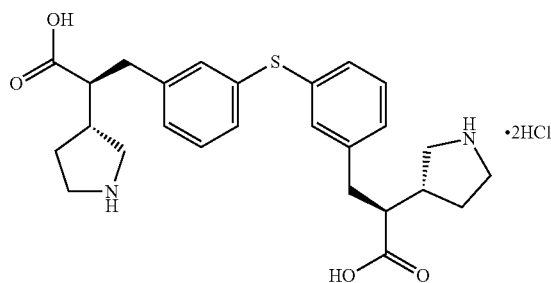 [SMILES: O=C(O)[C@@H](Cc1cccc(Sc2cccc(C[C@H](C(=O)O)[C@H]3CCNC3)c2)c1)[C@H]1CCNC1]

Prepare the title compound essentially as described in Example 6 using tert-butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenyl]sulfanylphenyl]methyl]-2-oxo-ethyl]pyrrolidine-1-carboxylate. Isolate the product by trituration with Et₂O. ES/MS (m/z): 469 (M+H).

EXAMPLE 11

(2S)-3-[3-[3-[(2S)-2-Carboxy-2-[(3R)-pyrrolidin-3-yl]ethyl]phenyl]sulfinylphenyl]-2-[(3R)-pyrrolidin-3-yl]propanoic acid; dihydrochloride

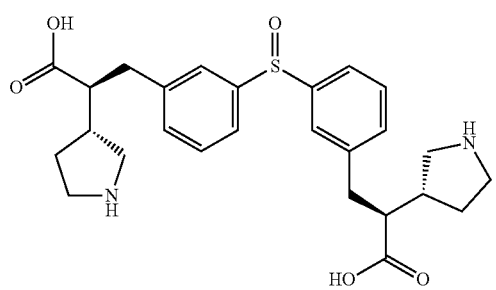

Prepare the title compound essentially as described in Example 6 using tert-butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenyl]sulfinylphenyl]methyl]-2-oxo-ethyl]pyrrolidine-1-carboxylate. Isolate the product by trituration with Et₂O followed by RP-HPLC/MS using the following parameters: column—Agilent ZORBAX Bonus RP; mobile phase—solvent A=0.05% trifluoroacetic acid in water (pH 2.5), solvent B=acetonitrile+0.05% trifluoroacetic acid; gradient—5 to 30% solvent B in solvent A; Flow Rate: 25 mL/min. Take up the product in a mixture of HCl (10% w/v aqueous) and water, then evaporate solvents under a stream of nitrogen at 40° C. ES/MS (m/z): 485 (M+H).

EXAMPLE 12

(2S)-3-[3-[3-[(2S)-2-Carboxy-2-[(3R)-pyrrolidin-3-yl]ethyl]phenyl]sulfonylphenyl]-2-[(3R)-pyrrolidin-3-yl]propanoicacid; dihydrochloride

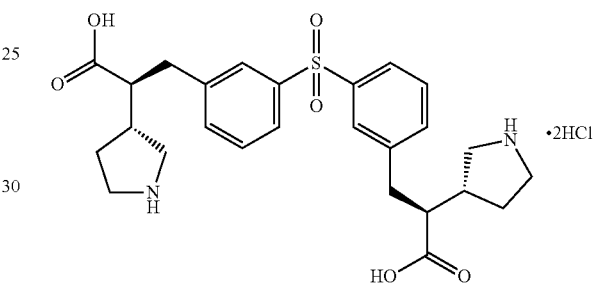

Prepare the title compound essentially as described in Example 6 using tert-butyl (3R)-3-[(1S)-2-tert-butoxy-1-[[3-[3-[(2S)-3-tert-butoxy-2-[(3R)-1-tert-butoxycarbonylpyrrolidin-3-yl]-3-oxo-propyl]phenyl]sulfonylphenyl]methyl]-2-oxo-ethyl]pyrrolidine-1-carboxylate. Isolate the product by trituration with Et₂O. ES/MS (m/z): 501 (M+H).

EXAMPLE 13

(2S)-3-[3-[[3-[(2S)-2-Carboxy-2-[(3R)-pyrrolidin-3-yl]ethyl]anilino]methyl]phenyl]-2-[(3R)-pyrrolidin-3-yl]propanoicacid; trihydrochloride

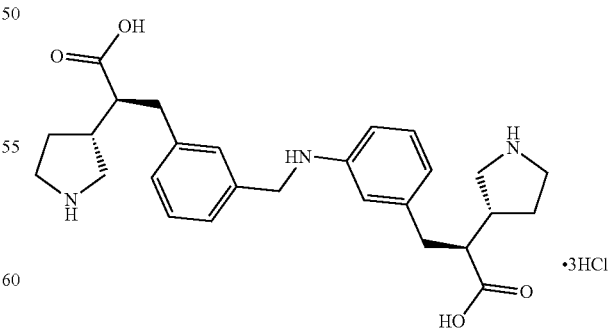

Prepare the title compound essentially as described in Example 6 using tert-butyl (3R)-3-[(1S)-2-tert-butoxy-1-[[3-[[3-[(2S)-3-tert-butoxy-2-[(3R)-1-tert-butoxycarbonylpyrrolidin-3-yl]-3-oxo-propyl]anilino]methyl]phenyl]

methyl]-2-oxo-ethyl]pyrrolidine-1-carboxylate. After decanting the product, purify by RP-HPLC/MS using the following parameters: column—Waters™ XBridge™ C18 (19×100 mm, 5 μm); mobile phase—solvent A=20 mM NH$_4$HCO$_3$ in water, solvent B=acetonitrile; flow rate 25 mL/min; gradient—5:95 to 25:75 B:A. Dissolve the purified material in aqueous HCl (1 N), stir at RT for 1 h, evaporate the solvent under a stream of nitrogen and dry the solid in-vacuo at 40° C. ES/MS (m/z): 466 (M+H).

EXAMPLE 14

(2S)-3-[3-[3-[(2S)-2-Carboxy-2-[(3R)-pyrrolidin-3-yl]ethyl]anilino]phenyl]-2-[(3R)-pyrrolidin-3-yl] propanoic acid; dihydrochloride

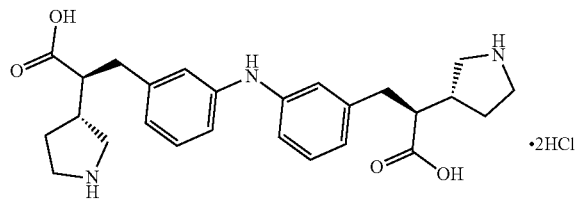 [SMILES: O=C(O)[C@@H](Cc1cccc(Nc2cccc(C[C@H](C(=O)O)[C@H]3CCNC3)c2)c1)[C@H]1CCNC1]

Mix (2S)-3-[3-[3-[(2S)-3-tert-butoxy-2-[(3R)-1-tert-butoxycarbonylpyrrolidin-3-yl]-3-oxo-propyl]anilino]phenyl]-2-[(3R)-1-tert-butoxycarbonylpyrrolidin-3-yl]propanoic acid (9 g, 12.7 mmol), isopropanol (27 mL), and HCl (5.5 M solution in isopropanol) and stir at RT for 2.5 h. Heat the reaction to 60° C. for 2.5 h, then cool to RT and stir for 3 days. Heat the reaction again to 60° C. for 2 h, cool to RT, and concentrate the reaction mixture in-vacuo to dryness. Triturate the solid residue with MTBE with sonication, filter and rinse with MTBE, then dry the solid in-vacuo. Mix the solid with concentrated aqueous HCl and heat to 80° C. overnight, then cool to RT and concentrate in-vacuo to dryness. Dissolve the residue in a minimal amount of water and adjust the pH to 7.5 by the addition of aqueous NaOH. Stir the mixture at RT for 3 h, then filter off the solid which precipitates. Dissolve the solid in aqueous HCl (1 N) and stir for 15 min at RT, then remove the water in-vacuo. Dry the residue in-vacuo at 45° C. overnight to give the title compound (5.4 g, 81%). ES/MS (m/z): 452 (M+H).

EXAMPLE 15

(2S)-3-[3-[3-[(2S)-2-carboxy-2-[(3R)-1-methylpyrrolidin-3-yl]ethyl]anilino]phenyl]-2-[(3R)-1-methylpyrrolidin-3-yl]propanoic acid; dihydrochloride

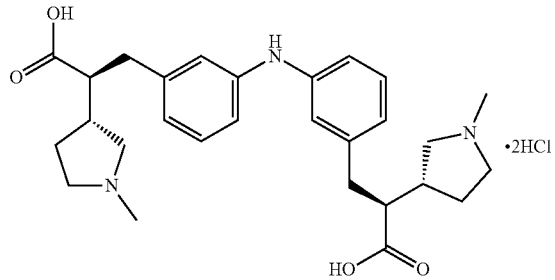 [SMILES: CN1CC[C@H]([C@H](Cc2cccc(Nc3cccc(C[C@H](C(=O)O)[C@H]4CCN(C)C4)c3)c2)C(=O)O)C1]

Add paraformaldehyde (89 mg, 0.95 mmol) to a suspension of (2S)-3-[3-[3-[(2S)-2-carboxy-2-[(3R)-pyrrolidin-3-yl]ethyl]anilino]phenyl]-2-[(3R)-pyrrolidin-3-yl]propanoic acid; dihydrochloride (100 mg, 0.19 mmol) in MeOH (1.9 mL). Stir at RT for 15 min. Add sodium triacetoxyborohydride (202 mg, 0.95 mmol) and stir at RT for 16 h. Concentrate the solution in-vacuo. Purify the residue with reverse phase chromatography (column: Claricep C-series silica-bound Cis) using a gradient of 5 to 25% acetonitrile in aqueous NH$_4$CO$_3$ (pH 9). Dissolve the purified material with aqueous hydrochloric acid (1 N, 1 mL) and stir at RT for 6 h. Concentrate the solution in-vacuo to obtain the title compound (30 mg, 27%). ES/MS (m/z): 480 (M+H).

EXAMPLE 16

(2S,2'S)-3,3'-[Sulfonylbis(azanediyl-3,1-phenylene)] bis{2-[(3R)-pyrrolidin-3-yl]propanoic acid}; dihydrochloride

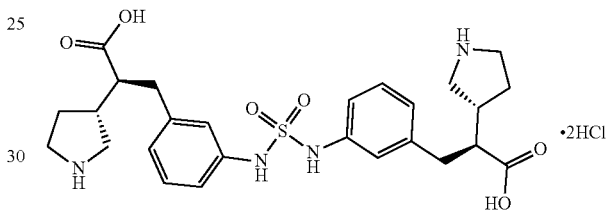

Prepare the title compound essentially as described in Example 6 using di-tert-butyl 3,3'-((2S,2'S)-((sulfonylbis (azanediyl))bis(3,1-phenylene))bis(3-(tert-butoxy)-3-oxopropane-1,2-diyl))(3R,3'R)-bis(pyrrolidine-1-carboxylate). ES/MS (m/z): 531 (M+H).

EXAMPLE 17

(2S)-3-Phenyl-2-[(3R)-pyrrolidin-3-yl]propanoic acid; hydrochloride

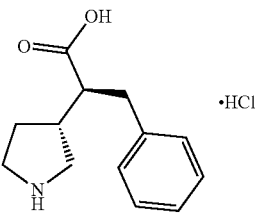 [SMILES: O=C(O)[C@@H](Cc1ccccc1)[C@H]1CCNC1 ; Cl]

Add HCl (5.5 M in isopropanol, 511 mL, 2.81 mol, 13 equiv) to a solution of (2S)-2-[(3R)-1-tert-butoxycarbonylpyrrolidin-3-yl]-3-phenyl-propanoic acid (69 g, 216 mmol) in isopropanol (207 mL) and stir at RT overnight. Dilute the mixture with a mixture of 2:1 MTBE:hexanes (900 mL) and stir for 10 min. Filter the suspension and wash the solid with 1:1 MTBE:hexanes (100 mL). Dry the solid in-vacuo at 50° C. to give the title compound (51.3 g, 93%) as a white solid. ES/MS (m/z): 220 (M+H).

EXAMPLE 18

(2R)-3-Phenyl-2-[(3S)-pyrrolidin-3-yl]propanoic acid; hydrochloride

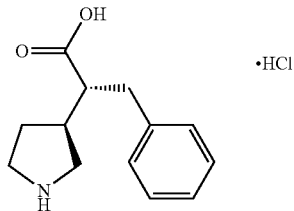 [SMILES: O=C(O)[C@H](Cc1ccccc1)[C@@H]1CCNC1 ; Cl]

Prepare the title compound essentially as described in Example 6 using (2R)-2-[(3 S)-1-tert-butoxycarbonylpyrrolidin-3-yl]-3-phenyl-propanoic acid. Stir the isolated product with HCl (2 M in ether) and water for 3 h, concentrate in-vacuo, then triturate with MTBE and dry in-vacuo at 40° C. ES/MS (m/z): 220 (M+H).

Synthesis of Radiolabeled and Cold (i.e. non-radiolabeled) Standard for in-vitro Apo(a) Binding Assay

Preparation 40

1-(3-Benzyloxyphenyl)imidazolidin-2-one

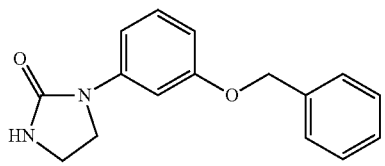 [SMILES: O=C1NCCN1c1cccc(OCc2ccccc2)c1]

Add argon-sparged DMF (20 mL) to a mixture of ethyleneurea (1.4 g, 16 mmol), 1-benzyloxy-3-iodobenzene (4.9 g, 16 mmol, 1.0 equiv), cuprous iodide (0.61 g, 3.1 mmol, 0.20 equiv), potassium dihydrogen phosphate (4.2 g, 31 mmol, 2.0 equiv). To the resulting suspension add N,N'-dimethylethylenediamine (0.33 mL, 0.28 g, 3.1 mmol, 0.20 equiv). Heat the blue suspension in a microwave reactor at 120° C. for 3 h. Cool the reaction and filter through a pad of silica gel, flushing the pad with EtOAc. Concentrate the filtrate. Purify the residue by silica gel chromatography using a gradient of 0 to 100% of 5:20:75 MeOH:acetone:EtOAc in hexanes to give the title compound (1.10 g, 26%) as a yellow solid. ES/MS (m/z): 269 (M+H)

Preparation 41

(2S)-3-[3-[3-(3-Benzyloxyphenyl)-2-oxo-imidazolidin-1-yl]phenyl]-2-[(3R)-1-tert-butoxycarbonylpyrrolidin-3-yl]propanoic acid

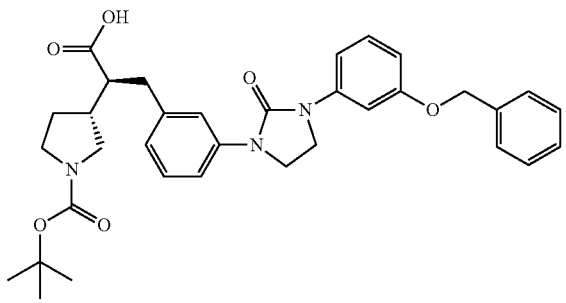 [SMILES: CC(C)(C)OC(=O)N1CC[C@H]([C@H](Cc2cccc(N3CCN(c4cccc(OCc5ccccc5)c4)C3=O)c2)C(=O)O)C1]

To a mixture of 1-(3-benzyloxyphenyl)imidazolidin-2-one (3.33 g, 12.4 mmol, 1.50 equiv) and ammonium; (2S)-3-(3-bromophenyl)-2-[(3R)-1-tert-butoxycarbonylpyrrolidin-3-yl]propanoate (3.30 g) under nitrogen atmosphere, add acetonitrile (41 mL) and DMF (to assist in solubility). Bubble a steady stream of argon through the suspension over 15 min. Add potassium carbonate (3.75 g, 26.8 mmol, 3.24 equiv), cuprous iodide (0.316 g, 1.66 mmol, 0.2 equiv) and N,N'-dimethylethylenediamine (0.360 mL, 3.31 mmol, 0.4 equiv). Heat the sealed vessel at 100° C. over the weekend. Add water and extract the aqueous layer with EtOAc twice. Acidify the aqueous phase with 0.5 N HCl in water and extract the aqueous layer with EtOAc, DCM and then EtOAc. Dry the combined organic phases over MgSO$_4$, filter and evaporate to dryness. Purify the residue by silica gel chromatography using a gradient of 10 to 60% (1% acetic acid/acetone) in hexanes to give the title compound (4 g, 82%). ES/MS (m/z): 486 (M+H—BOC).

Preparation 42 tert-Butyl (3R)-3-[(1S)-1-[[3-[3-(3-benzyloxyphenyl)-2-oxo-imidazolidin-1-yl]phenyl]methyl]-2-tert-butoxy-2-oxo-ethyl]pyrrolidine-1-carboxylate

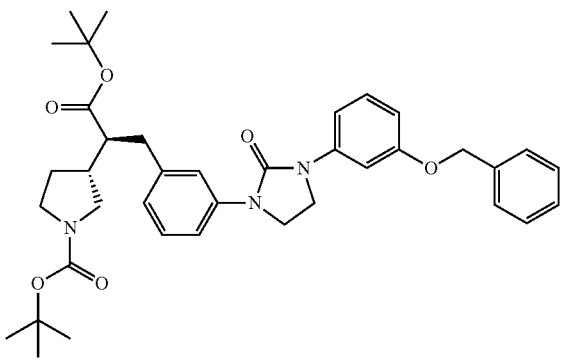 [SMILES: CC(C)(C)OC(=O)[C@@H](Cc1cccc(N2CCN(c3cccc(OCc4ccccc4)c3)C2=O)c1)[C@H]1CCN(C(=O)OC(C)(C)C)C1]

To a solution of (2S)-3-[3-[3-(3-benzyloxyphenyl)-2-oxo-imidazolidin-1-yl]phenyl]-2-[(3R)-1-tert-butoxycarbonylpyrrolidin-3-yl]propanoic acid (4.0 g, 6.8 mmol) in toluene (68 mL) at 70° C. add N,N-dimethylformamide di-tert-butyl acetal (15 mL, 55 mmol, 8.0 equiv) and heat the reaction at 70° C. overnight. Purify the residue by silica gel chromatography using a gradient of 0 to 50% EtOAc in hexanes to give the title compound (1.56 g, 33%). ES/MS (m/z): 542 (M+H—BOC).

Preparation 43 tert-Butyl (3R)-3-[(1S)-2-tert-butoxy-1-[[3-[3-(3-hydroxyphenyl)-2-oxo-imidazolidin-1-yl]phenyl]methyl]-2-oxo-ethyl]pyrrolidine-1-carboxylate

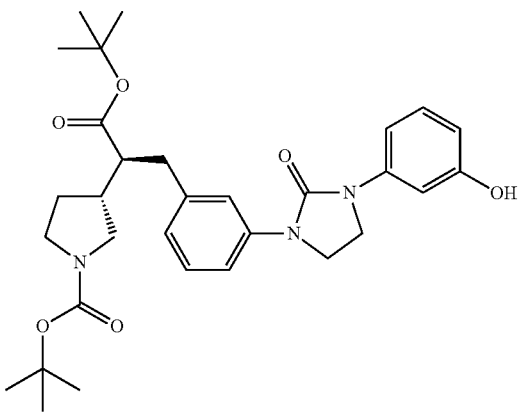 [SMILES: CC(C)(C)OC(=O)[C@@H](Cc1cccc(N2CCN(c3cccc(O)c3)C2=O)c1)[C@H]1CCN(C(=O)OC(C)(C)C)C1]

Dissolve tert-butyl (3R)-3-[(1S)-1-[[3-[3-(3-benzyloxyphenyl)-2-oxo-imidazolidin-1-yl]phenyl]methyl]-2-tert-butoxy-2-oxo-ethyl]pyrrolidine-1-carboxylate (1.56 g, 2.43 mmol) in THF (80 mL) and add palladium hydroxide (0.7 g, 0.99 mmol, 0.41 equiv). Degas the reaction under vacuum and then expose to hydrogen gas three times. Stir the reaction at RT under hydrogen (1 atm) for 4 h. Concentrate the reaction and purify the residue by silica gel chromatography using a gradient of 0 to 50% EtOAc in hexanes to obtain the title compound (1.19 g, 87%). ES/MS (m/z): 452 (M+H—BOC).

Preparation 44 tert-Butyl (3R)-3-[(1S)-2-tert-butoxy-2-oxo-1-[[3-[2-oxo-3-[3-(tritritiomethoxy)phenyl]imidazolidin-1-yl]phenyl]methyl]ethyl]pyrrolidine-1-carboxylate

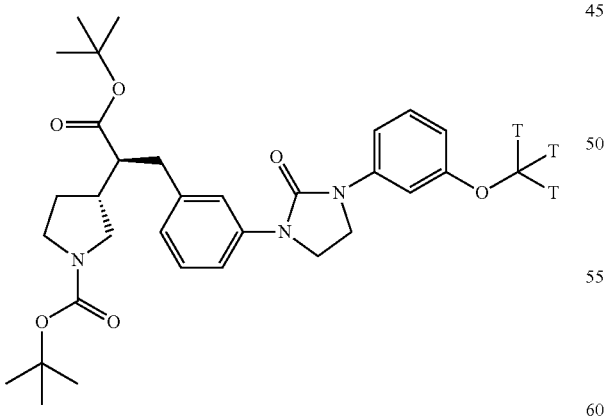

To a solution of tert-butyl (3R)-3-[(1S)-2-tert-butoxy-1-[[3-[3-(3-hydroxyphenyl)-2-oxo-imidazolidin-1-yl]phenyl]methyl]-2-oxo-ethyl]pyrrolidine-1-carboxylate (4 mg, 0.007 mmol) in DMF (0.5 mL) add cesium carbonate (10 mg, 0.03 mmol). Stir the solution at RT for 10 minutes. Add [3H] methyl nosylate (50 mCi) and stir at RT for 1.5 h. Purify the reaction mixture by RP-HPLC/MS using the following parameters: column—Phenomenex® Gemini® C18 (250× 10 mm); mobile phase—solvent A=water+trifluoroacetic acid (0.1%), solvent B=acetonitrile+trifluoroacetic acid (0.1%); gradient—50 to 100% B in A over 50 minutes; flow rate—3 mL/min. Dissolve the purified product in EtOH and carry forward to Preparation 45 without further characterization.

Preparation 45

(2S)-3-[3-[2-Oxo-3-[3-(tritritiomethoxy)phenyl]imidazolidin-1-yl]phenyl]-2-[(3R)-pyrrolidin-3-yl]propanoicacid; hydrochloride

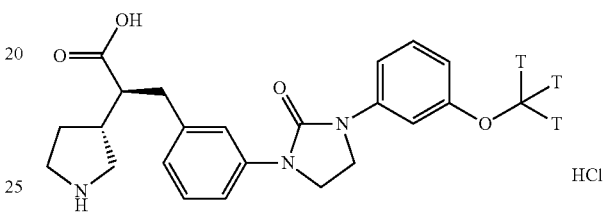

Remove the solvent from tert-butyl (3R)-3-[(1S)-2-tert-butoxy-2-oxo-1-[[3-[2-oxo-3-[3-(tritritiomethoxy)phenyl] imidazolidin-1-yl]phenyl]methyl]ethyl]pyrrolidine-1-carboxylate in-vacuo and dissolve the residue in hydrogen chloride (4M solution in 1,4-dioxane). Stir the mixture at RT overnight. Purify the reaction mixture by RP-HPLC/MS using the following parameters: column—Phenomenex® Gemini® C18 (250×10 mm); mobile phase—solvent A=water+trifluoroacetic acid (0.1%), solvent B=acetonitrile+trifluoroacetic acid (0.1%); gradient—10 to 70% B in A over 60 minutes; flow rate—3 mL/min. Dissolve the purified product in ethanol. Mass spectrometry gives a spectrum that is consistent with the inactive material [ES/MS (m/z): 410 (M+H)] and a specific activity of 63 Ci/mmol.

Preparation 46

1-(3-Methoxyphenyl)imidazolidin-2-one

Prepare the title compound essentially as described for Preparation 40 using 1-iodo-3methoxybenzene and potassium phosphate tribasic as the base. Use conventional heating to heat the reaction to 120° C. for 16 h. Workup the reaction by diluting with EtOAc, filtering through a pad of Celite®, washing the organics with water, aqueous NH₄OH, and saturated aqueous NaCl. Purify the crude material by silica gel chromatography using a gradient of 20 to 100% EtOAc in hexanes. ES/MS (m/z): 193 (M+H).

Preparation 47

(2S)-2-[(3R)-1-tert-Butoxycarbonylpyrrolidin-3-yl]-3-[3-[3-(3-methoxyphenyl)-2-oxo-imidazolidin-1-yl]phenyl]propanoicacid

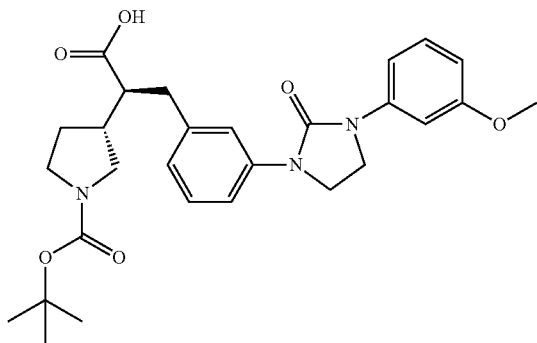 [SMILES: COc1cccc(N2CCN(c3cccc(C[C@H](C(=O)O)[C@H]4CCN(C(=O)OC(C)(C)C)C4)c3)C2=O)c1]

Mix (2S)-3-(3-bromophenyl)-2-[(3R)-1-tert-butoxycarbonylpyrrolidin-3-yl]propanoic acid (190 mg, 0.4770 mmol), 1-(3-methoxyphenyl)imidazolidin-2-one (0.2751 g, 1.431 mmol, 3 equiv), [(2-di-tert-butylphosphino-2',4',6'-triisopropyl-1,1'-biphenyl)-2-(2'-amino-1,1'-biphenyl)] palladium(II) methanesulfonate (tBuXPhos-Pd-G3, 0.0379 g, 0.0477 mmol, 0.1 equiv) and sodium tert-butoxide (0.1418 g, 1.431 mmol, 3 equiv) in 1,4-dioxane (4.8 mL) and stir the mixture under nitrogen atmosphere at 100° C. overnight. Dilute the mixture with EtOAc and acidify with an aqueous solution of HCl (1 N). Filter the mixture through a pad of Celite®, separate the layers, and dry the organics over MgSO$_4$. Filter and concentrate the organics, then purify the residue by reverse-phase flash chromatography (silica-bound C18 column) using a gradient of 40 to 70% acetonitrile in aqueous NH$_4$CO$_3$ (pH 9) to give the title compound (70 mg, 28%) as a white solid. Obtain an additional amount of the title compound (90 mg, 36%) by RP-HPLC/MS using the following parameters: column—Waters™ XBridge™ C18 (19×100 mm, 5 µm); mobile phase—solvent A=20 mM NH$_4$HCO$_3$ in water, solvent B=acetonitrile; flow rate 25 mL/min; gradient—30:70 to 50:50 B:A. ES/MS (m/z): 510 (M+H).

Preparation 48

(2S)-3-[3-[2-Oxo-3-[3-(methoxy)phenyl]imidazolidin-1-yl]phenyl]-2-[(3R)-pyrrolidin-3-yl]propanoic acid; hydrochloride

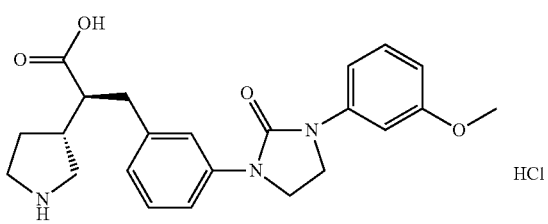 [SMILES: COc1cccc(N2CCN(c3cccc(C[C@H](C(=O)O)[C@H]4CCNC4)c3)C2=O)c1 ; Cl]

Prepare the title compound essentially as described in Preparation 45 using (2S)-2-[(3R)-1-tert-butoxycarbonylpyrrolidin-3-yl]-3-[3-[3-(3-methoxyphenyl)-2-oxo-imidazolidin-1-yl]phenyl]propanoic acid. ES/MS (m/z): 410 (M+H).

Biological Assays

In Vitro Apo(a) Binding Assay

The in vitro binding affinity of compounds to the intended target human Apo(a) protein is tested in a competitive binding assay. Human Apo(a) protein containing 17 Kringle repeats is affinity purified from conditioned media of transiently transfected HEK-293F cells. All reagents are prepared in assay buffer containing 50 mM Tris-HCl pH 7.4, 0.1% BSA. The binding assay is conducted by adding to each well of a clear-bottom plate 50 each of (1) test compound in dilution series (final concentration 0.3210000 nM), (2) Apo(a) protein (6 ng/well), (3) re-suspended Wheat Germ Agglutinin Polyvinyltoluene SPA beads (20 mg/ml), and (4) the radioligand, tritium-labeled (2S)-3-[3-[2-oxo-3-[3-(tritritiomethoxy)phenyl]imidazolidin-1-yl]phenyl]-2-[(3R)-pyrrolidin-3-yl]propanoic acid; hydrochloride (final concentration 0.52 nM). Plates are incubated for 60 minutes at RT and counted on TRILUX LSC. Non-specific binding, defined as binding in the presence of 10 M cold (i.e. non-radiolabeled) ligand: (2S)-3-[3-[2-oxo-3-[3-(methoxy)phenyl]imidazolidin-1-yl]phenyl]-2-[(3R)-pyrrolidin-3-yl]propanoic acid; hydrochloride is subtracted to determine specific binding. Data are analyzed by fitting to a standard single site binding model and the IC$_{50}$ for the Example test compound is determined. These results are summarized in Table 1, and indicate that the Example test compounds bind to human Apo(a) protein. Inhibition of the assembly of the LDL particle with apo(a) through binding to the Apo(a) protein supports a reduction in Lp(a) levels.

TABLE 1

| Example | IC$_{50}$* (nM) |
| --- | --- |
| 1 | <0.314 (n = 1) |
| 3 | 2.13 ± 0.159 (n = 2) |
| 6 | <0.314 (n = 1) |
| 14 | <0.314 (n = 1) |
| 17 | 152 ± 21.3 (n = 2) |
| 18 | 126 ± 5.97 (n = 2) |

*Geometric Mean ± SEM (n)

In Vitro Lp(a) Assembly Assay

The ability of compounds to inhibit the formation of Lp(a) particles in vitro is assessed by a cell-free assembly assay. Conditioned media (DMEM supplemented with 10% FBS, 20 mM HEPES, and 1× penicillin/streptomycin) is collected from confluent wild-type HepG2 cells (a source of endogenously expressed ApoB) and from a HEK293 stable cell line expressing human Apo(a) protein containing 17 Kringle repeats (selected on 1 mg/ml geneticin) after 24 hours of culture at 37° C. and 5% CO$_2$. An in vitro assembly assay is conducted by combining equal parts of HepG2 and HEK293 conditioned media with the test compounds added in dilution series (final concentration 0.01~100 nM). The reaction is incubated at 37° C. for 2 hrs and then stopped with the addition of 6-aminocaproic acid (EACA) to a final concentration of 150 mM. Lp(a) is detected using a sandwich ELISA with an anti-Lp(a) capture antibody and an HRP-conjugated anti-ApoB detection antibody. The ELISA is developed using TMB, stopped using 1 N sulfuric acid, and the signal is read at 450 nm on a Molecular Devices plate reader. The % inhibition of Lp(a) formed for each test condition is determined with an assembly reaction having no inhibitor present (with matched DMSO concentration at 1%) set to 0% inhibition, and an assembly reaction with a minimal amount of the HepG2 conditioned media present (50-fold dilution) set to 100% inhibition. Data are fitted to a 4-parameter curve to determine the $IC_{50}$ values summarized in Table 2. Addition of the Example test compound to conditioned media containing ApoB and Apo(a) leads to concentration-dependent inhibition of Lp(a) formation in vitro, as summarized in Table 2. The results indicate that these compounds inhibit the assembly of Lp(a) from Apo(a) and the LDL particle.

TABLE 2

| Example | $IC_{50}$* (nM) |
|---|---|
| 1 | 0.0963 ± 0.0233 (n = 9) |
| 3 | 0.934 ± 0.306 (n = 2) |
| 5 | 0.17 ± 0.0124 (n = 4) |
| 6 | 0.108 ± 0.0149 (n = 4) |
| 7 | 0.372 ± 0.0464 (n = 8) |
| 8 | 0.288 ± 0.19 (n = 4) |
| 9 | 0.359 ± 0.0292 (n = 2) |
| 10 | 0.36 ± 0.119 (n = 4) |
| 11 | 0.396 ± 0.241 (n = 4) |
| 12 | 0.235 ± 0.0509 (n = 2) |
| 13 | 2.39 ± 0.61 (n = 2) |
| 14 | 0.348 ± 0.0984 (n = 13) |
| 15 | 54.6 ± 9.15 (n = 3) |
| 16 | 0.563 ± 0.119 (n = 2) |
| 17 | 1690 ± 402 (n = 43) |
| 18 | 635 ± 165 (n = 9) |

*Geometric Mean ± SEM (n)

In Vivo Lp(a) Inhibition in Mice

The ability of compounds to reduce steady-state Lp(a) level in vivo is assessed in a transgenic mouse model capable of producing humanized Lp(a) particles. In vivo effects of Lp(a) disruptor compounds are tested in 7 to 17-month-old female double transgenic mice expressing human apoB-100 and human apo(a) containing 17 Kringle repeats: B6.SJL-Tg(APOB)1102Sgy Tg(Alb-LPA)32Arte. Mice are housed with standard light cycle (12 hrs. light/12 hrs. dark), at RT 72±8° F. and relative humidity of 30–70%, and with free access to water and normal chow diet (Harlan Tecklad diet 2014). Mice are randomized to treatment groups (n=5/group) 3 to 5 days before the study by body weight and baseline plasma Lp(a) concentration using BRAT (Block Randomized Allocation Tool) for the study. Mice are orally dosed (or subcutaneously where noted) with vehicle (oral dose vehicle: 10 mL/kg, 1% HEC, 0.25% Tween80, 0.01% Antifoam; subcutaneous dose vehicle: 5 mL/kg saline) or test compound at various dose levels twice a day (6:30 am and 3:30 μm) for 5 days. Blood is collected in heparin-coated capillary tubes via tail bleed. Twenty μL of each blood sample is transferred to a DBS card (Whatman Cat #: WB12 9243) for drug exposure analysis. The remaining blood samples are centrifuged to separate plasma. Lp(a) concentration in plasma is measured using a sandwich ELISA as described for the in vitro Lp(a) assembly assay. The % inhibition for each dose group is determined with the mean the Lp(a) level of the vehicle control group set to 0% inhibition. Table 3 shows results from dose response studies wherein tail bleed samples are taken on day 3 at 8 h post morning oral dose. $ED_{50}$ (effective dose for 50% Lp(a) inhibition) calculations as determined by Threshold Minimum Effective Dose analysis. Table 4 shows results from single dose studies wherein tail bleed samples are taken on day 3 at 4 h (or 8 h where noted) post morning oral dose (or subcutaneous dose where noted). These results shown in Tables 3 and 4 demonstrate that the compounds are efficacious at reducing plasma Lp(a) levels in vivo, supporting a proposition that the compounds can be used to reduce the Lp(a) plasma concentration.

TABLE 3

| Example | $ED_{50}$ (mg/kg)[1] | Lp(a) inhibition (% at 30 mpk)[2] |
|---|---|---|
| 1 | 3.3 ± 0.53 | 91 ± 0.73 |
| 14 | 14.6 ± 2.48 | 72 ± 2.23 |
| 17 | 20.6 ± 1.79 | 60 ± 3.46 |
| 18 | 7.6 ± 2.43 | 68 ± 1.82 |

[1]$ED_{50}$ ± standard error
[2]Mean ± SEM

TABLE 4

| Example | Dose (mg/kg) | Lp(a) inhibition (%)[1] |
|---|---|---|
| 5 | 3 | 43.8 ± 4.24 |
| 7 | 30[2] | 44.6 ± 5.0 |
| 9 | 30 | 56.5 ± 2.77 |
| 10 | 30 | 43.6 ± 4.6 |
| 12 | 30 | 50 ± 3.82[3] |

[1]Mean ± SEM
[2]Subcutaneous dosing
[3]Samples taken at 8 h post oral dosing.

We claim:
1. A compound of the formula:

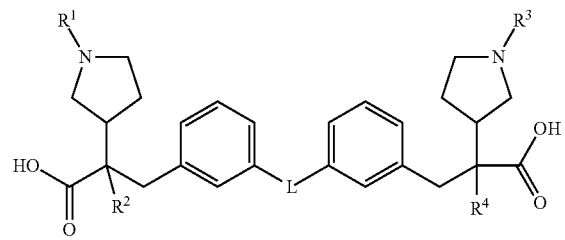

wherein
L is selected from the group consisting of —CH$_2$NHCH$_2$—, —CH$_2$NH—, —NH—, —S—, —S(O)—, —S(O)$_2$—, —O—, —OCH$_2$—, —OCH$_2$CH$_2$O—, —NHSO$_2$NH—,

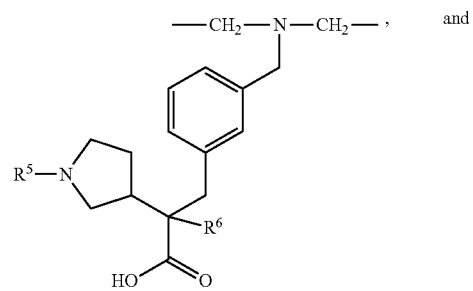

and

-continued

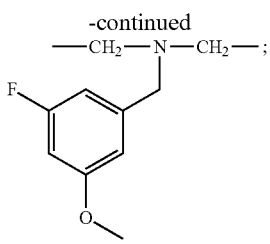

$R^1$, $R^2$, $R^3$, $R^4$, $R^5$, and $R^6$ are each independently selected from the group consisting of H and $CH_3$;

or a pharmaceutically acceptable salt thereof.

2. A compound as claimed by claim 1 wherein $R^1$ is H, and $R^3$ is H; or a pharmaceutically acceptable salt thereof.

3. A compound a claimed by claim 1 wherein $R^5$ is H, or a pharmaceutically acceptable salt thereof.

4. A compound as claimed by claim 1 wherein $R^2$ is H and $R^4$ is H; or a pharmaceutically acceptable salt thereof.

5. A compound as claimed by claim 1 wherein $R^6$ is H, or a pharmaceutically acceptable salt thereof.

6. A compound as claimed by claim 1 wherein $R^2$ is $CH_3$ and $R^4$ is $CH_3$; or a pharmaceutically acceptable salt thereof.

7. A compound as claimed by claim 1 wherein $R^2$ is $CH_3$, $R^4$ is $CH_3$, and $R^6$ is $CH_3$, or a pharmaceutically acceptable salt thereof.

8. A compound as claimed by claim 1 wherein L is selected from the group consisting of —$CH_2NHCH_2$—, —$CH_2NH$—, —NH—, —S—, —S(O)—, —$S(O)_2$—, —O—, —$OCH_2$—, —$OCH_2CH_2O$—, and —$NHSO_2NH$—; or a pharmaceutically acceptable salt thereof.

9. A compound as claimed by claim 1 wherein L is

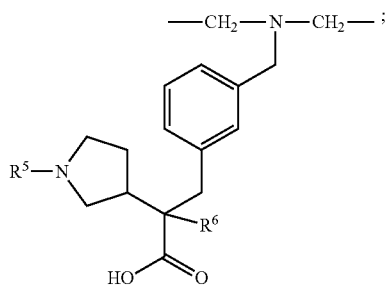

or a pharmaceutically acceptable salt thereof.

10. A compound as claimed by claim 1 wherein the compound is:

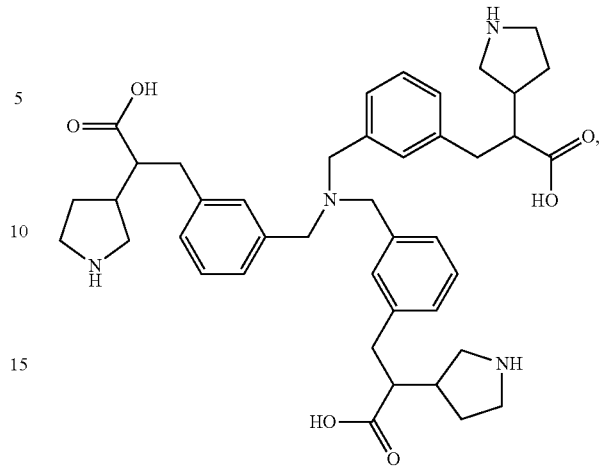

or a pharmaceutically acceptable salt thereof.

11. A compound as claimed by claim 10 wherein the compound is

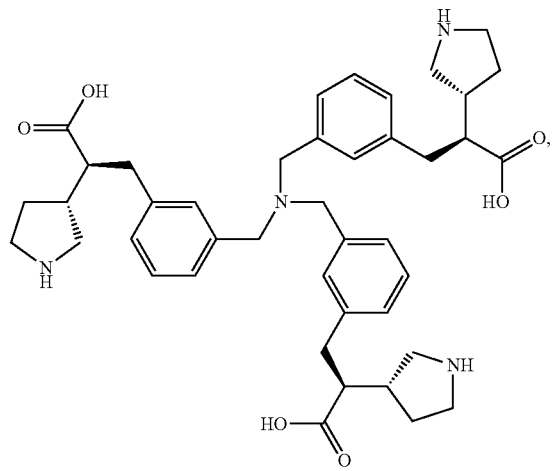 [SMILES: O=C(O)[C@@H](Cc1cccc(CN(Cc2cccc(C[C@H](C(=O)O)[C@H]3CCNC3)c2)Cc2cccc(C[C@H](C(=O)O)[C@H]3CCNC3)c2)c1)[C@H]1CCNC1]

or a pharmaceutically acceptable salt thereof.

12. A compound as claimed by claim 11, wherein the compound is a hydrochloride salt.

13. A compound as claimed by claim 12 wherein the compound is a tetrahydrochloride salt.

14. A pharmaceutical composition comprising a compound as claimed by claim 1, or a pharmaceutically acceptable salt thereof, and at least one pharmaceutically acceptable carrier, diluent, or excipient.

15. A composition as claimed by claim 14 for use in the treatment of elevated Lp(a) plasma levels in a patient in need thereof.

16. A method for treating elevated Lp(a) plasma levels in a patient in need thereof, comprising administering an effective amount of a compound as claimed by claim 1, or a pharmaceutically acceptable salt thereof.

* * * * *

UNITED STATES PATENT AND TRADEMARK OFFICE
CERTIFICATE OF CORRECTION

PATENT NO. : 11,286,249 B2
APPLICATION NO. : 17/056144
DATED : March 29, 2022
INVENTOR(S) : Celia Lafuente Blanco et al.

It is certified that error appears in the above-identified patent and that said Letters Patent is hereby corrected as shown below:

In the Claims

Claim 3, Column 61, Line 20 (Approx.): delete "a" and insert -- as --.

Signed and Sealed this
Thirty-first Day of January, 2023

Katherine Kelly Vidal
*Director of the United States Patent and Trademark Office*